United States Patent
Chuang et al.

(10) Patent No.: US 9,748,729 B2
(45) Date of Patent: Aug. 29, 2017

(54) 183NM LASER AND INSPECTION SYSTEM

(71) Applicant: KLA-Tencor Corporation, Milpitas, CA (US)

(72) Inventors: Yung-Ho Alex Chuang, Cupertino, CA (US); J. Joseph Armstrong, Fremont, CA (US); Yujun Deng, Pleasanton, CA (US); Vladimir Dribinski, Livermore, CA (US); John Fielden, Los Altos, CA (US); Jidong Zhang, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 92 days.

(21) Appl. No.: 14/872,890

(22) Filed: Oct. 1, 2015

(65) Prior Publication Data

US 2016/0099540 A1  Apr. 7, 2016

Related U.S. Application Data

(60) Provisional application No. 62/059,368, filed on Oct. 3, 2014.

(51) Int. Cl.
*G02F 1/39* (2006.01)
*H01S 3/109* (2006.01)
(Continued)

(52) U.S. Cl.
CPC ......... *H01S 3/109* (2013.01); *G01N 21/9501* (2013.01); *G01N 21/956* (2013.01);
(Continued)

(58) Field of Classification Search
CPC . G02F 1/3532; G02F 1/37; G02F 1/39; G02F 2001/354; H01S 3/0092; H01S 3/109; H01S 5/0092
See application file for complete search history.

(56) References Cited

U.S. PATENT DOCUMENTS 3,755,704 A  8/1973  Spindt et al.
4,178,561 A  12/1979  Hon et al.
(Continued)

FOREIGN PATENT DOCUMENTS

CN  101702490 A  5/2010
DE  102007004235 B3  1/2008
(Continued)

OTHER PUBLICATIONS

Saikawa et al., "52 mJ narrow-bandwidth degenerated optical parametric system with a large-aperture periodically poled MgO:LiNbO3 device", Optics Letters, 31 (#21), 3149-3151 (2006).
(Continued)

*Primary Examiner* — Daniel Petkovsek
(74) *Attorney, Agent, or Firm* — Bever, Hoffman & Harms, LLP

(57) ABSTRACT

A laser assembly for generating laser output light at an output wavelength of approximately 183 nm includes a fundamental laser, an optical parametric system (OPS), a fifth harmonic generator, and a frequency mixing module. The fundamental laser generates fundamental light at a fundamental frequency. The OPS generates a down-converted signal at a down-converted frequency. The fifth harmonic generator generates a fifth harmonic of the fundamental light. The frequency mixing module mixes the down-converted signal and the fifth harmonic to produce the laser output light at a frequency equal to a sum of the fifth harmonic frequency and the down-converted frequency. The OPS generates the down-converted signal by generating a down-converted seed signal at the down-converted frequency, and then mixing the down-converted seed signal with a portion of the fundamental light. At least one of the frequency mixing, frequency conversion or harmonic gen-
(Continued)

eration utilizes an annealed, deuterium-treated or hydrogen-treated CLBO crystal.

13 Claims, 16 Drawing Sheets

(51) Int. Cl.
- *G02B 21/10* (2006.01)
- *G02B 21/16* (2006.01)
- *G02B 21/36* (2006.01)
- *H01S 3/10* (2006.01)
- *H01S 3/108* (2006.01)
- *H01S 5/00* (2006.01)
- *H01S 5/06* (2006.01)
- *H01S 5/40* (2006.01)
- *G01N 21/95* (2006.01)
- *G01N 21/956* (2006.01)

(52) U.S. Cl.
CPC ............. *G02B 21/10* (2013.01); *G02B 21/16* (2013.01); *G02B 21/361* (2013.01); *H01S 3/10007* (2013.01); *H01S 3/1083* (2013.01); *H01S 3/10084* (2013.01); *H01S 5/0071* (2013.01); *H01S 5/0085* (2013.01); *H01S 5/0604* (2013.01); *H01S 5/4012* (2013.01); *G01N 2021/95676* (2013.01)

(56) References Cited

U.S. PATENT DOCUMENTS

| | | |
|---|---|---|
| 4,467,189 A | 8/1984 | Tsuchiya |
| 4,644,221 A | 2/1987 | Gutierrez et al. |
| 4,853,595 A | 8/1989 | Alfano et al. |
| 5,120,949 A | 6/1992 | Tomasetti |
| 5,144,630 A * | 9/1992 | Lin ............... G02F 1/3532 372/21 |
| 5,563,702 A | 10/1996 | Emery et al. |
| 5,572,598 A | 11/1996 | Wihl et al. |
| 5,742,626 A | 4/1998 | Mead et al. |
| 5,760,809 A | 6/1998 | Malhotra et al. |
| 5,760,899 A | 6/1998 | Eismann |
| 5,825,562 A | 10/1998 | Lai et al. |
| 5,999,310 A | 12/1999 | Shafer et al. |
| 6,064,759 A | 5/2000 | Buckley et al. |
| 6,201,257 B1 | 3/2001 | Stettner et al. |
| 6,201,601 B1 | 3/2001 | Vaez-Iravani et al. |
| 6,212,310 B1 | 4/2001 | Waarts et al. |
| 6,220,914 B1 | 4/2001 | Lee et al. |
| 6,249,371 B1 | 6/2001 | Masuda et al. |
| 6,271,916 B1 | 8/2001 | Marxer et al. |
| 6,285,018 B1 | 9/2001 | Aebi et al. |
| 6,373,869 B1 * | 4/2002 | Jacob ............... G02F 1/3534 359/326 |
| 6,498,801 B1 | 12/2002 | Dudelzak et al. |
| 6,535,531 B1 | 3/2003 | Smith et al. |
| 6,590,698 B1 | 7/2003 | Ohtsuki et al. |
| 6,608,676 B1 | 8/2003 | Zhao et al. |
| 6,816,520 B1 | 11/2004 | Tulloch et al. |
| 6,859,335 B1 | 2/2005 | Lai et al. |
| 6,888,855 B1 | 5/2005 | Kopf |
| 7,098,992 B2 | 8/2006 | Ohtsuki et al. |
| 7,136,402 B1 | 11/2006 | Ohtsuki |
| 7,313,155 B1 | 12/2007 | Mu |
| 7,321,468 B2 | 1/2008 | Herkommer et al. |
| 7,339,961 B2 | 3/2008 | Tokuhisa et al. |
| 7,345,825 B2 | 3/2008 | Chuang et al. |
| 7,352,457 B2 | 4/2008 | Kvamme et al. |
| 7,432,517 B2 | 10/2008 | Botma et al. |
| 7,463,657 B2 | 12/2008 | Spinelli et al. |
| 7,471,705 B2 | 12/2008 | Gerstenberger et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,593,437 B2 | 9/2009 | Staroudoumov et al. |
| 7,593,440 B2 | 9/2009 | Spinelli et al. |
| 7,609,309 B2 | 10/2009 | Brown et al. |
| 7,623,557 B2 | 11/2009 | Tokuhisa et al. |
| 7,627,007 B1 | 12/2009 | Armstrong et al. |
| 7,643,529 B2 | 1/2010 | Brown et al. |
| 7,715,459 B2 | 5/2010 | Brown et al. |
| 7,813,406 B1 | 10/2010 | Nguyen et al. |
| 7,822,092 B2 | 10/2010 | Ershov et al. |
| 7,875,948 B2 | 1/2011 | Hynecek et al. |
| 7,920,616 B2 | 4/2011 | Brown et al. |
| 7,952,633 B2 | 5/2011 | Brown et al. |
| 7,999,342 B2 | 8/2011 | Hsu et al. |
| 8,208,505 B2 | 6/2012 | Dantus et al. |
| 8,238,647 B2 | 8/2012 | Ben-Yishay et al. |
| 8,298,335 B2 | 10/2012 | Armstrong |
| 8,319,960 B2 | 11/2012 | Aiko et al. |
| 8,391,660 B2 | 3/2013 | Islam |
| 8,503,068 B2 | 8/2013 | Sakuma |
| 8,514,587 B2 | 8/2013 | Zhang et al. |
| 8,629,384 B1 | 1/2014 | Biellak et al. |
| 8,665,536 B2 | 3/2014 | Armstrong |
| 8,686,331 B2 | 4/2014 | Armstrong |
| 8,755,417 B1 | 6/2014 | Dribinski |
| 8,873,596 B2 | 10/2014 | Dribinski |
| 8,891,079 B2 | 11/2014 | Zhao et al. |
| 8,896,917 B2 | 11/2014 | Armstrong |
| 8,929,406 B2 | 1/2015 | Chuang et al. |
| 8,976,343 B2 | 3/2015 | Genis |
| 9,318,869 B2 * | 4/2016 | Chuang ............... H01S 3/1083 |
| 2001/0000977 A1 | 5/2001 | Vaez-Iravani et al. |
| 2002/0109110 A1 | 8/2002 | Some et al. |
| 2002/0114553 A1 | 8/2002 | Mead et al. |
| 2002/0191834 A1 | 12/2002 | Fishbaine |
| 2003/0043876 A1 | 3/2003 | Lublin et al. |
| 2003/0147128 A1 | 8/2003 | Shafer et al. |
| 2003/0161374 A1 | 8/2003 | Lokai |
| 2004/0080741 A1 | 4/2004 | Marxer et al. |
| 2005/0041702 A1 | 2/2005 | Fermann et al. |
| 2005/0110988 A1 | 5/2005 | Nishiyama et al. |
| 2005/0111081 A1 | 5/2005 | Shafer et al. |
| 2005/0122021 A1 | 6/2005 | Smith et al. |
| 2005/0128473 A1 | 6/2005 | Karpol et al. |
| 2005/0157382 A1 | 7/2005 | Kafka et al. |
| 2005/0190452 A1 | 9/2005 | Govorkov et al. |
| 2005/0254049 A1 | 11/2005 | Zhao |
| 2005/0254065 A1 | 11/2005 | Stokowski |
| 2006/0038984 A9 | 2/2006 | Vaez-Iravani et al. |
| 2006/0171656 A1 | 8/2006 | Adachi et al. |
| 2006/0239535 A1 | 10/2006 | Takada |
| 2006/0291862 A1 | 12/2006 | Kawai |
| 2007/0002465 A1 | 1/2007 | Chuang et al. |
| 2007/0047600 A1 | 3/2007 | Luo et al. |
| 2007/0096648 A1 | 5/2007 | Nakajima et al. |
| 2007/0103769 A1 | 5/2007 | Kuwabara |
| 2007/0146693 A1 | 6/2007 | Brown et al. |
| 2007/0188744 A1 | 8/2007 | Leslie et al. |
| 2007/0211773 A1 | 9/2007 | Gerstenberger et al. |
| 2007/0263680 A1 | 11/2007 | Staroudoumov et al. |
| 2008/0173903 A1 | 7/2008 | Imai et al. |
| 2008/0182092 A1 | 7/2008 | Bondokov et al. |
| 2008/0186476 A1 | 8/2008 | Kusunose |
| 2008/0204737 A1 | 8/2008 | Ogawa |
| 2009/0084989 A1 | 4/2009 | Imai |
| 2009/0108207 A1 | 4/2009 | Liu |
| 2009/0128912 A1 | 5/2009 | Okada |
| 2009/0180176 A1 | 7/2009 | Armstrong et al. |
| 2009/0185583 A1 | 7/2009 | Kuksenkov et al. |
| 2009/0185588 A1 | 7/2009 | Munroe |
| 2009/0296755 A1 | 12/2009 | Brown et al. |
| 2010/0103409 A1 | 4/2010 | Ohshima et al. |
| 2010/0188655 A1 | 7/2010 | Brown et al. |
| 2010/0301437 A1 | 12/2010 | Brown et al. |
| 2011/0062127 A1 | 3/2011 | Gu et al. |
| 2011/0073982 A1 | 3/2011 | Armstrong et al. |
| 2011/0085149 A1 | 4/2011 | Nathan |
| 2011/0101219 A1 | 5/2011 | Uchiyama et al. |
| 2011/0134944 A1 | 6/2011 | Kaneda et al. |

(56) References Cited

U.S. PATENT DOCUMENTS

| | | |
|---|---|---|
| 2011/0222565 A1 | 9/2011 | Horain et al. |
| 2011/0228263 A1 | 9/2011 | Chuang et al. |
| 2011/0279819 A1 | 11/2011 | Chuang et al. |
| 2012/0026578 A1 | 2/2012 | Sakuma |
| 2012/0033291 A1 | 2/2012 | Kneip |
| 2012/0092657 A1 | 4/2012 | Shibata |
| 2012/0113995 A1 | 5/2012 | Armstrong |
| 2012/0120481 A1 | 5/2012 | Armstrong |
| 2012/0137909 A1 | 6/2012 | Hawes et al. |
| 2012/0160993 A1 | 6/2012 | Nevet et al. |
| 2012/0314286 A1 | 12/2012 | Chuang et al. |
| 2013/0009069 A1 | 1/2013 | Okada |
| 2013/0016346 A1 | 1/2013 | Romanovsky et al. |
| 2013/0020491 A1 | 1/2013 | Mazzillo |
| 2013/0021602 A1 | 1/2013 | Dribinski et al. |
| 2013/0064259 A1 | 3/2013 | Wakabayashi et al. |
| 2013/0077086 A1 | 3/2013 | Chuang et al. |
| 2013/0082241 A1 | 4/2013 | Kub et al. |
| 2013/0088706 A1 | 4/2013 | Chuang et al. |
| 2013/0126705 A1 | 5/2013 | Maleev |
| 2013/0169957 A1 | 7/2013 | Wolf et al. |
| 2013/0176552 A1 | 7/2013 | Brown et al. |
| 2013/0194445 A1 | 8/2013 | Brown et al. |
| 2013/0264481 A1 | 10/2013 | Chern et al. |
| 2013/0313440 A1* | 11/2013 | Chuang ............... G01N 21/956 250/372 |
| 2013/0336574 A1 | 12/2013 | Nasser-Ghodsi et al. |
| 2014/0016655 A1 | 1/2014 | Armstrong |
| 2014/0034816 A1 | 2/2014 | Chuang et al. |
| 2014/0050234 A1 | 2/2014 | Ter-Mikirtychev |
| 2014/0071520 A1 | 3/2014 | Armstrong |
| 2014/0111799 A1 | 4/2014 | Lei et al. |
| 2014/0153596 A1 | 6/2014 | Chuang et al. |
| 2014/0158864 A1 | 6/2014 | Brown et al. |
| 2014/0204963 A1 | 7/2014 | Chuang et al. |
| 2014/0226140 A1 | 8/2014 | Chuang et al. |
| 2014/0291493 A1 | 10/2014 | Chuang et al. |
| 2014/0305367 A1 | 10/2014 | Chuang et al. |
| 2015/0007765 A1 | 1/2015 | Dribinski |
| 2015/0177159 A1 | 6/2015 | Brown et al. |
| 2015/0200216 A1 | 7/2015 | Muramatsu et al. |
| 2015/0268176 A1 | 9/2015 | Deng |
| 2015/0275393 A1 | 10/2015 | Bondokov et al. |
| 2015/0294998 A1 | 10/2015 | Nihtianov |
| 2015/0372446 A1 | 12/2015 | Chuang et al. |

FOREIGN PATENT DOCUMENTS

| | | |
|---|---|---|
| EP | 0532927 A2 | 3/1993 |
| EP | 0746871 B1 | 5/2000 |
| EP | 0602983 B1 | 6/2000 |
| EP | 1194804 B1 | 7/2003 |
| EP | 1939917 A2 | 7/2008 |
| EP | 2013951 A2 | 1/2009 |
| JP | H0511287 A | 1/1993 |
| JP | H08241977 A | 9/1996 |
| JP | H11121854 A | 4/1999 |
| JP | 2000223408 A | 8/2000 |
| JP | 2002033473 | 1/2002 |
| JP | 2002-258339 A | 9/2002 |
| JP | 2003043533 A | 2/2003 |
| JP | 2005275095 A | 10/2005 |
| JP | 2006-60162 A | 3/2006 |
| JP | 200786108 | 4/2007 |
| JP | 2007-206452 A | 8/2007 |
| JP | 2007249092 A | 9/2007 |
| JP | 2007298932 A | 11/2007 |
| JP | 2009058782 A | 3/2009 |
| JP | 2009-145791 A | 7/2009 |
| JP | 2010003755 A | 1/2010 |
| JP | 2010-54547 A | 3/2010 |
| JP | 2010-256784 A | 11/2010 |
| JP | 2011-23532 A | 2/2011 |
| JP | 2011-128330 A | 6/2011 |
| WO | 9532518 A1 | 11/1995 |
| WO | 9617372 A1 | 6/1996 |
| WO | 2003/069263 A2 | 8/2003 |
| WO | 2005/022705 A2 | 3/2005 |
| WO | 2009/082460 A2 | 7/2009 |
| WO | 2010/037106 A2 | 4/2010 |
| WO | 2012/154468 A2 | 11/2012 |
| WO | 2013/015940 A2 | 1/2013 |
| WO | 2013006867 A1 | 1/2013 |
| WO | 2014067754 A2 | 5/2014 |

OTHER PUBLICATIONS

Sakuma et al., "True CW 193.4-nm light generation based on frequency conversion of fiber amplifiers", Optics Express 19 (#16), 15020-15025 (2011).

Sakuma et al., "High power, narrowband, DUV laser source by frequency mixing in CLBO", Advanced High-Power Lasers and Applications, Nov. 2000, pp. 7-14, Ushio Inc.

Mead et al., "Solid-state lasers for 193-nm photolithography", Proc. SPIE 3051, Optical Microlithography X, pp. 882-889 (Jul. 7, 1997).

Zavartsev et al. "High efficient diode pumped mixed vanadate crystal Nd:Gd0.7Y0.3VO4 laser", International Conference on Lasers, Applications, and Technologies 2007: Advanced Lasers and Systems, Valentin A. Orlovich et al. ed., Proc. of SPIE vol. 6731, 67311P (2007), 5 pages.

International Search Report and Written Opinion dated May 13, 2014 for PCT/US2014/012902, filed Jan. 24, 2014 in the name of KLA-Tencor Corporation.

Dianov et al. "Bi-doped fiber lasers: new type of high-power radiation sources", Conference on Lasers and Electro-Optics, May 6-11, 2007, 2 pages.

Kalita et al. "Multi-watts narrow-linewidth all fiber Yb-doped laser operating at 1179 nm", Optics Express, 18 (6), pp. 5920-5925 (2010).

Kashiwagi et al. "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).

Sasaki et al. "Progress in the growth of a CsLiB6O10 crystal and its application to ultraviolet light generation", Optical Materials, vol. 23, 343-351 (2003).

Shirakawa et al. "High-power Yb-doped photonic bandgap fiber amplifier at 1150-1200nm", Optics Express 17 (2), 447-454 (2009).

Ter-Mikirtychev et al. "Tunable LiF:F2—color center laser with an intracavity integrated-optic output coupler", Journal of Lightwave Technology, 14 (10), 2353-2355 (1996).

Yoo et al. "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.

International Search Report and Written Opinion dated Jul. 11, 2014 for PCT/US2014/030989, filed Mar. 18, 2014 in the name of KLA-Tencor Corporation.

International Search Report and Written Opinion dated May 20, 2014 for PCT/US2014/016198, filed Feb. 13, 2014 in the name of KLA-Tencor Corporation.

File history for U.S. Appl. No. 11/735,967, filed Apr. 16, 2007 by Vladimir L. Dribinski et al.

KLA-Tencor Corporation, U.S. Appl. No. 14/248,045, filed Apr. 8, 2014 and entitled "Passivation of Nonlinear Optical Crystals".

KLA-Tencor Corporation, U.S. Appl. No. 62/059,368, filed Oct. 3, 2014 and entitled "183nm Laser and Inspection System".

KLA-Tencor Corpoation, U.S. Appl. No. 14/210,355, filed Mar. 13, 2014 and entitled "193nm Laser and an Inspection System Using a 193nm Laser".

Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.

Herriott, et al., "Folded Optical Delay Lines", Applied Optics 4, #8, pp. 883-889 (1965).

(56) References Cited

OTHER PUBLICATIONS

Herriott, et al., "Off-Axis Paths in Spherical Mirror Interferometers", Applied Optics 3, #4, pp. 523-526 (1964).

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 μm", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l. Conf. Centre, Endiburgh, Scotland, UK, Sep. 15-19, 2008, Piscataway, NJ: IEEE, US, pp. 278-281.

Fu, Xiaoqian, "Higher Quantum Efficiency by Optimizing GaN Photocathode Structure", 978-1-4244-6644-3/10/ © 2010 IEEE, pp. 234-235.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Fanton et al, Multiparameter Measurements of Thin Film . . . , Journal of Applied Physics, vol. 73, No. 11, p. 7035 (1993).

Fowler, R. H., et al, Electron Emission in Intense Electric Fields, Mar. 31, 1928, 9 pgs.

Koike, AkifumiField Emitter Equipped With a Suppressor to Control Emission Angel, IEEE Electron Device Letters, vol. 34, No. 5, May 2013, 3 pgs.

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Neo, YoichiroElectron Optical Properties of Microcolumn with Field Emitter, JJAP 52 (2013) 036603, 5 pgs.

Rakhshandehroo, M.R. et al, Fabrication of a self-aligned silicon field emission . . . , JVSTB, 16, 765 (1998); doi: 10.1116/1,589900, 6 pgs.

Rakhshandehroo, M.R. et al, Field emission from gated Si emitter tips with precise . . . , JVSTB, 15, 2777 (1997); doi: 10.1116/1.589726, 6 pgs.

Sato, T., et al, Fabrication and characterization of HfC coated . . . , J. Vac. Sci. Technol. B 2194), published Jul. 31, 2003, 5 pgs.

Serbun Pavel et al, Stable field emission of single B-doped . . . , JVSTB, 31, 02B101 (2013); doi: 10.1116/1.4765088, 7 pgs.

Utsumi, TakaoVacuum Microelectrnoics: What's New and Exciting, IEEE vol. 38, No. 10, Oct. 1991, 8 pgs.

\* cited by examiner

| Fundamental laser type | Nd:Vandate, Nd:YAG, Yb-doped fiber | | Yb-doped fiber | |
|---|---|---|---|---|
| Harmonic | Fundamental (short) | Fundamental (long) | Fundamental (short) | Fundamental (long) |
| $\omega$ | 1064.0 | 1065.0 | 1029.0 | 1031.0 |
| $\omega_s$ | 1307 | 1299 | 1652 | 1626 |
| $2\omega$ | 532.0 | 532.5 | 514.5 | 515.5 |
| $4\omega$ | 266.0 | 226.3 | 257.3 | 257.8 |
| $5\omega$ | 212.8 | 213 | 205.8 | 206.2 |
| $5\omega + \omega_s$ | 183 | 183 | 183 | 183 |

Figure 3

183NM LASER AND INSPECTION SYSTEM

PRIORITY APPLICATION

The present application claims priority to U.S. Provisional Patent Application 62/059,368 entitled "183 NM LASER AND INSPECTION SYSTEM", filed by Chuang et al. on Oct. 3, 2014.

RELATED APPLICATION

The present application is related to U.S. patent application Ser. No. 13/797,939, entitled "Solid-State Laser and Inspection System Using 193 nm Laser", filed on Mar. 12, 2013 by Chuang et al. and incorporated by reference herein.

BACKGROUND OF THE DISCLOSURE

Field of the Disclosure

This disclosure relates to a laser and specifically to a solid state or fiber laser that generates radiation near 183 nm and is suitable for use in inspection of photomasks, reticles, and/or wafers. The laser is preferably a pulsed laser such as a Q-switched laser or a mode-locked laser. This disclosure further relates to an inspection system using a laser operating at a wavelength near 183 nm.

Related Art

Excimer lasers for generating light at 193 nm are well known in the art. Unfortunately, such lasers are not well suited to inspection applications because of their low laser pulse repetition rates and their use of toxic and corrosive gases in their lasing medium, which leads to high cost of ownership.

Solid state and fiber lasers for generating light near 193 nm are also known. Exemplary lasers use two different fundamental wavelengths (e.g. US 2014/0111799 by Lei et al.) or the eighth harmonic of the fundamental (e.g. U.S. Pat. No. 7,623,557 to Tokuhisa et al.), either of which requires lasers or materials that are expensive or are not in high volume production. Another approach (U.S. Pat. No. 5,742,626 to Mead et al.) has not resulted in a commercial product with stable output and high power as required for semiconductor inspection applications (approximately 1 W or more is typically required in a laser that can run continuously for three or more months between service events). Moreover, most of these lasers have very low power output and are limited to laser pulse repetition rates of a few MHz or less.

As semiconductor devices dimensions shrink, the size of the largest particle or pattern defect that can cause a device to fail also shrinks. Hence a need arises for detecting smaller particles and defects on patterned and unpatterned semiconductor wafers. The intensity of light scattered by particles smaller than the wavelength of that light generally scales as a high power of the dimensions of that particle (for example, the total scattered intensity of light from an isolated small spherical particle scales proportional to the sixth power of the diameter of the sphere and inversely proportional to the fourth power of the wavelength). Because of the increased intensity of the scattered light, shorter wavelengths will generally provide better sensitivity for detecting small particles and defects than longer wavelengths.

Since the intensity of light scattered from small particles and defects is generally very low, high illumination intensity is required to produce a signal that can be detected in a very short time. Average light source power levels of 1 W or more may be required. At these high average power levels, a high pulse repetition rate is desirable as the higher the repetition rate, the lower the energy per pulse and hence the lower the risk of damage to the system optics or the article being inspected. High repetition rates are also desirable in high-speed inspection as a high repetition rate (such as about 50 MHz or higher) allows many pulses to be collected for each image resulting in less sensitivity to pulse-to-pulse variations in intensity.

Therefore, a need arises for a laser and preferably to a solid state or fiber laser that generates radiation shorter than 193 nm and is suitable for use in inspection of photomasks, reticles, and/or wafers. Notably, such inspections at high speeds often require minimum laser pulse repetition rates of multiple MHz (e.g. greater than 50 MHz in some cases).

SUMMARY OF THE DISCLOSURE

The present invention is directed to a laser assembly and associated method for generating 183 nm laser light using a fundamental laser by way of generating and mixing a fifth harmonic of the fundamental laser light with a down-converted signal, wherein the down-converted signal is produced by way of generating a low-power down-converted seed signal having a required down-converted frequency, and then mixing the down-converted seed signal with a portion of the fundamental laser light to produce the down-converted signal at a peak power level that is ten or more times greater than the down-converted seed signal. In addition to efficiencies associated with utilizing fifth harmonic light to generate the 183 nm output laser light, the two-step approach for generating the down-converted signal in accordance with the present invention provides several advantages over conventional methodologies. First, the initial step of generating the lower power down-converted seed signal facilitates avoiding distortion and damage to the optical components utilized to generate the higher power down-converted signal by way of minimizing the exposure of these components to high power idler frequencies having wavelengths longer than about 4 μm, which are absorbed by most non-linear crystals in a way that causes distortion and/or damage. Second, generating the down-converted seed signal at a relatively low power facilitates greater control over the down-converted frequency, which in turn facilitates fine tuning of the 183 nm laser output light. Another advantage of the present invention is that it facilitates the manufacture of 183 nm laser assemblies using a wide variety of components, thereby providing manufacturing flexibility by way of allowing the manufacturer to select and utilize components that are readily available and/or are relatively inexpensive at the time of manufacture. For example, the various described embodiments generate 183 nm laser output light by way of mixing a selected fundamental frequency (e.g., having corresponding fundamental wavelengths of approximately 1064 nm or approximately 1030 nm) with a corresponding down-converted signal frequency (e.g., having corresponding down-converted wavelengths in the range of approximately 1250 nm to approximately 1420 nm, or in the range of approximately 1400 nm to approximately 1830 nm). Fundamental lasers capable of generating at least one of these fundamental frequencies are typically readily available at reasonable prices in various combinations of power and repetition rate. Because an optical parametric system (OPS) generates the down-converted signal in a manner that facilitates controlling the down-converted signal frequency, the present invention allows a manufacturer to select the lowest priced or most readily available fundamental laser for a given manufacturing run with full confidence that the 183 nm laser output light will be produced.

According to an embodiment of the present invention, laser assembly includes a fundamental laser, an optical parametric system (OPS), a fifth harmonic generator and a frequency mixing module. The fundamental laser configured to generate fundamental light having a fundamental wavelength (e.g., equal to one of approximately 1064 nm, approximately 1053 nm, approximately 1047 nm, or approximately 1030 nm) and a corresponding fundamental frequency. The OPS is optically coupled to the fundamental laser such that the OPS receives a first portion of the fundamental light, and is configured to generate the down-converted signal having the required down-converted frequency $\omega_s$. In one embodiment, the required down-converted frequency ($\omega_s$) is lower than the fundamental frequency ($\omega$) and higher than 50% of the fundamental frequency (i.e., $0.5\omega < \omega_s < \omega$). The fifth harmonic generator receives a second portion of the fundamental light and, optionally, also receives a fourth harmonic, and is configured to generate fifth harmonic light (i.e., having a fifth harmonic frequency ($5\omega$) equal to five times the fundamental frequency). The frequency mixing module is optically coupled to receive the down-converted signal from the OPS and the fifth harmonic light from the fifth harmonic generator, and configured to generate the 183 nm laser output light by way of operably mixing the down-converted signal and the fifth harmonic light. In accordance with the present invention, the OPS includes a down-converted seed signal generator (e.g., a seed laser or an optical parametric oscillator) that is configured to generate a down-converted seed signal at a required down-converted frequency and at a relatively low (first) peak power level, and an optical parametric amplifier (OPA) configured such that the down-converted seed signal and a portion of the fundamental light are mixed by passing once through a non-linear crystal, thereby generating the down-converted signal at the down-converted frequency and at a (second) peak power level that ten times (or more) higher than that of the down-converted seed signal. The OPS is also configured to generate the down-converted signal at an appropriate down-converted frequency and peak power level such that a sum of the down-converted frequency and said fifth harmonic frequency produces said laser output light in the range of approximately 180 nm to approximately 185 nm.

In alternative embodiments, the fundamental laser is configured to generate fundamental light at a fundamental frequency having a corresponding wavelength equal to one of approximately 1064 nm, approximately 1053 nm, approximately 1047 nm, and approximately 1030 nm, and the OPS is configured to generate the down-converted signal at a down-converted signal frequency and corresponding wavelength that, when mixed with the fifth harmonic of the fundamental frequency (e.g., approximately 1250 nm to 1420 nm for a fundamental wavelength of approximately 1064 nm), produces laser output light at approximately 183 nm. By way of further example, when the fundamental wavelength is approximately 1030 nm, the down-converted signal is generated with a wavelength of approximately 1400 nm to 1830 nm, and for fundamental lasers of approximately 1047 nm or approximately 1053 nm wavelength, the down-converted signal is generated with a wavelength between about 1290 nm and 1580 nm. In alternative embodiments, the laser assemblies for generating an output wavelength of approximately 183 nm described herein utilize fundamental lasers that are Q-switched lasers, mode-locked lasers, or quasi-continuous-wave lasers. Because near non-critical phase matching is used in the final frequency mixing module, that final conversion stage is efficient and is relatively insensitive to small misalignments allowing stable output at power levels in the range of about 1 W to 20 W or more.

In one embodiment, at least one of the fifth harmonic generator and the frequency mixing module includes an annealed, hydrogen-treated or deuterium-treated cesium lithium borate (CLBO) crystal that is configured to be nearly non-critically phase matched for generating a wavelength near 183 nm by mixing a wavelength between about 206 nm and 213 nm with an infra-red wavelength. Because of the near non-critical phase matching, the frequency mixing is very efficient (e.g. the non-linear coefficient can be approximately, or slightly larger than, 1 pm $V^{-1}$) and the walk-off angle small (e.g. less than about 30 mrad). In a preferred embodiment, the annealed CLBO crystal is held at a constant temperature near 50° C.

According to exemplary embodiments, the down-converted seed signal generator is configured to generate the down-converted seed signal at a lower (first) average power level in the range of 1 mW to 500 mW, and the OPA is configured to generate the higher power down-converted signal at a (second) power level in the range of 1 W to 20 W (or higher). In one exemplary embodiment, the down-converted seed signal generator of the OPS is implemented using a diode laser that directly generates the down-converted seed signal, and in the other exemplary embodiment the down-converted seed signal generator is implemented using an optical parametric oscillator (OPO) that is configured to generate the down-converted seed signal by way of converting a portion of the fundamental light. In both exemplary embodiments, the OPA of the optical parametric system includes a beam combiner configured to combine the first fundamental light portion with the down-converted seed signal, a non-linear crystal configured to amplify the down-converted seed signal by stimulated down-conversion of the first portion of said fundamental light, and a beam splitter (wavelength separator) configured to separate the down-converted signal from unwanted frequencies. In a presently preferred embodiment, the non-linear crystals utilized in the OPS (e.g., in the OPA and optional OPO) are implemented using periodically polled non-linear optical crystals (e.g., periodically polled non-linear optical crystals formed from lithium niobate (LN), magnesium-oxide doped lithium niobate (Mg:LN), stoichiometric lithium tantalate (SLT), magnesium-oxide doped stoichiometric lithium tantalate (Mg:SLT), or potassium titanyl phosphate (KTP)).

According to an alternative embodiment of the invention, 183 nm laser output light is generated by mixing fifth harmonic light with a down-converted signal in a manner similar to that described above, but in this case the down-converted signal is generated by down-converting a second harmonic of the fundamental laser light (i.e., instead of down-converting light at the fundamental frequency). When fundamental laser light having a wavelength of 1064 nm is used, the second harmonic light comprises light in the visible green spectrum (i.e., the second harmonic light has wavelength of 532 nm), whereby the generation of down-converted signal using a "green-pumped" OPO avoids the heating problems associated with generating 1.3 μm down-converted signals from 1064 nm fundamental light (i.e., distortion/damage to non-linear crystals in the OPS caused by the absorption of idler signals having wavelengths greater than 4 μm), thus obviating the need for generating the lower power seed signal utilized in the embodiments described above. However, the generation of a 1.3 μm down-converted signal by down-converting 532 nm light produces other issues that restrict the type of non-linear crystals usable in the "green-pumped" OPO (i.e., the currently preferred non-linear crystal is LBO), and the down-conversion process is less efficient.

Also disclosed herein are systems and methods for inspecting an article such as a semiconductor wafer, a photomask, or a reticle. These systems and methods include a laser generating an output wavelength near 183 nm using near non-critical phase matching in the final frequency summation stage.

In addition to their shorter wavelength, the 183 nm lasers of the present invention have several advantages compared with 193 nm lasers. Compared with lasers that generate 193 nm as the sixth or eighth harmonic, the 183 nm lasers of the present invention have the advantage of using fundamental wavelengths that are readily available at power levels of tens to hundreds of W. An advantage compared with lasers that generate 193 nm by mixing a fifth harmonic with a signal frequency is that frequency mixing module of the 183 nm laser is more efficient because CLBO is nearly non-critically phase matched for generating 183 nm from a fifth harmonic wavelength in the range of approximately 206 nm to approximately 213 nm. This allows more efficient conversion of the signal frequency and the fifth harmonic into the final output and also makes the frequency mixing module more stable. An another advantage is that for a signal frequency having a corresponding wavelength between about 1.25 µm and about 1.83 µm significantly more energy goes into the signal compared with the idler, thereby resulting in more efficient conversion of fundamental power (compared with a signal wavelength near 2.1 µm where almost equal amounts of power must go into the signal and the idler).

BRIEF DESCRIPTION OF THE DRAWINGS

FIG. 3 shows a table of exemplary wavelengths generated by and mixed within the 183 nm laser assemblies of FIG. 1A to generate 183 nm laser output light in accordance with alternative embodiments of the present invention.

DETAILED DESCRIPTION OF THE DRAWINGS

The present invention relates to an improvement in inspection systems utilized in the semiconductor fabrication industry, and in particular to laser assemblies for such inspection systems that are capable of generating laser light having an average output wavelength in the range of approximately 180 nm to approximately 185 nm (e.g., approximately 183 nm) and having an average light source power level of 1 W or more in a manner that avoids the problems associated with prior art approaches. The following description is presented to enable one of ordinary skill in the art to make and use the invention as provided in the context of a particular application and its requirements. Note that in the following description, where a wavelength is mentioned without qualification, that wavelength may be assumed to be the wavelength in vacuo.

Figure 1A:
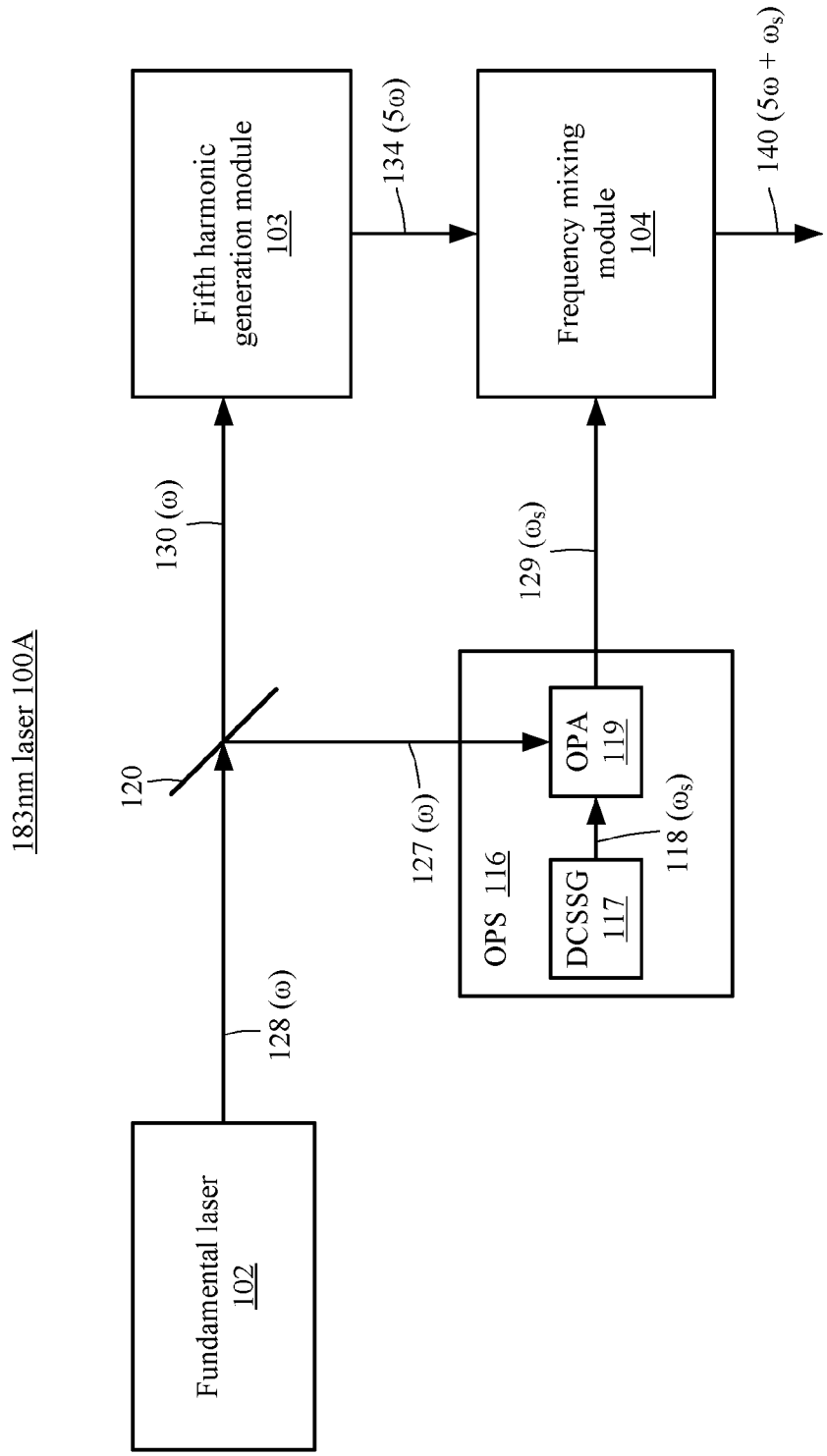
FIGS. 1A and 1B are simplified block diagrams showing exemplary 183 nm laser assemblies according to alternative exemplary embodiments of the present invention.
Figure 1B:
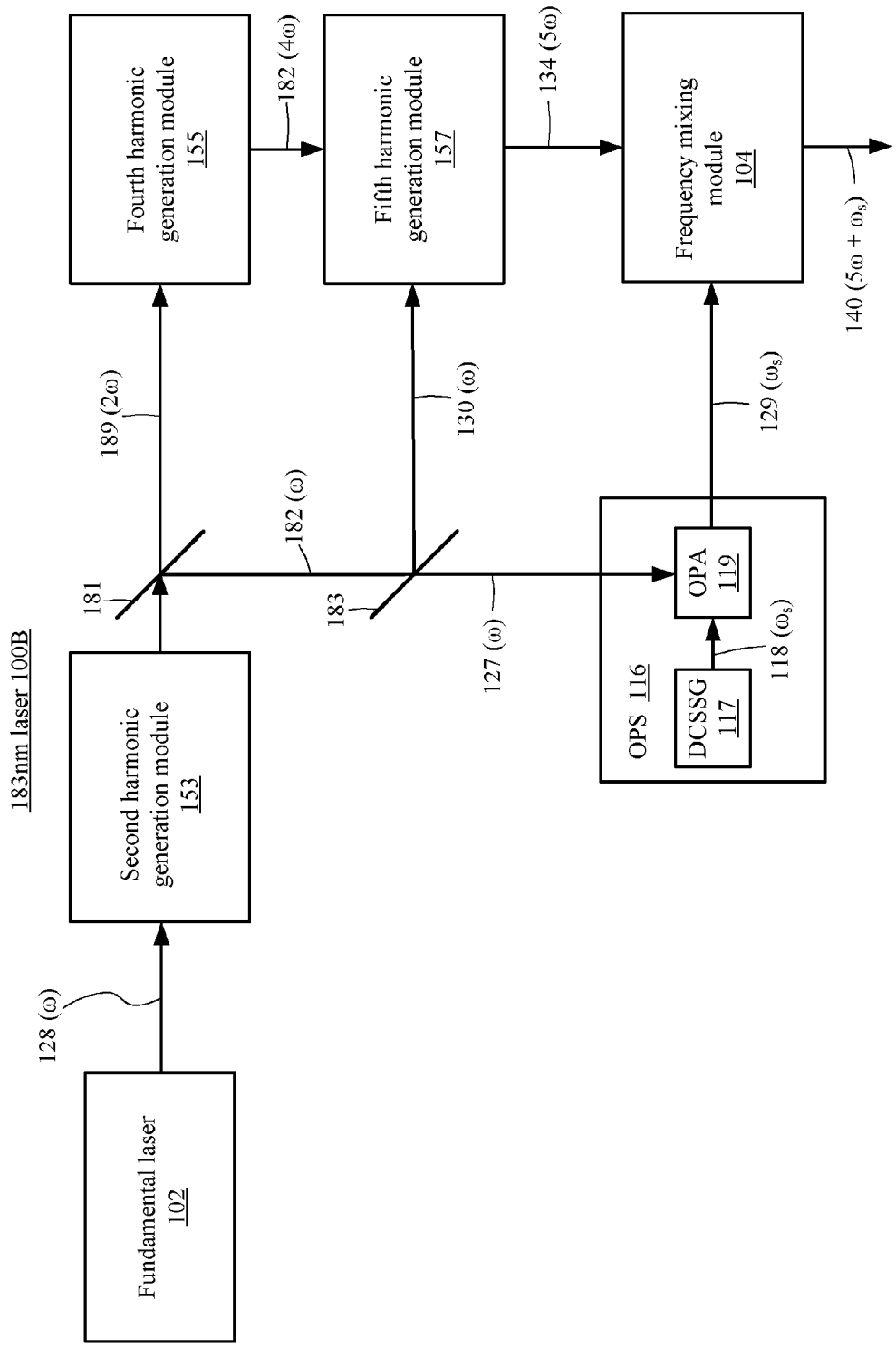

FIGS. 1A and 1B are simplified block diagrams showing 183 nm laser assemblies 100A and 100B, respectively, according to alternative exemplary embodiments of the present invention. Although laser assemblies 100A and 100B differ in certain respects, each laser assembly 100A and 100B utilize substantially the same set of core optical components—that is, each of laser assembly 100A and 100B includes a fundamental laser 102, an optical parametric system (OPS) 116, a fifth harmonic generator (which is identified using "103" in FIG. 1A and "157" in FIG. 1B for reasons explained below), and a frequency mixing module 104 that are arranged and configured to generate laser output light 140 having a frequency in the range of approximately 180 nm to approximately 185 nm, and most preferably approximately 183 nm. Note that these core components are identified by the same or similar reference numbers in each of FIGS. 1A and 1B to indicate that these core components are configured and function in the same or a similar manner in each of the two exemplary embodiments. Specifically, in each embodiment fundamental laser 102 is configured to generate fundamental light 128 having a fundamental wavelength (e.g., approximately 1064 nm) and a corresponding fundamental frequency ω. Similarly, in each embodiment, OPS 116 is optically coupled to fundamental laser 102 such that OPS 116 receives as input light a portion 127 of fundamental light 128, and OPS 116 is configured to generate a down-converted signal 129. In a similar manner, fifth harmonic generator 103 is optically coupled to fundamental laser 102 such that fifth harmonic generator 103 receives as input light at least a portion 130 of the fundamental light 128, and fifth harmonic generator 103 is configured to generate fifth harmonic light 134 at a fifth harmonic frequency 5ω equal to five times fundamental frequency ω. Frequency mixing module 104 is optically coupled to receive as input light both down-converted signal 129 from OPS 116 and fifth harmonic light 134 from fifth harmonic generator 103, and is configured to generate laser output light 140 by way of mixing down-converted signal 129 and fifth harmonic light 134.

According to an aspect of the present invention, OPS 116 utilizes a down-converted seed signal generator 117 (e.g., a diode laser or an OPO) and an optical parametric amplifier (OPA) 119 to generate down-converted signal 129 at a down-converted frequency $\omega_s$ such that, when mixed with fifth harmonic light 134 in frequency mixing module 104, produces laser output light 140 at the desired wavelength (i.e., in the range of approximately 180 nm to approximately 185 nm). Specifically, down-converted seed signal generator 117 is configured to generate a down-converted seed signal 118 having the same down-converted frequency $\omega_s$ as down-converted signal 129, but having a lower (first) peak power level that is substantially lower than that of down-converted signal 129. As used herein, the phrase "down-converted" is intended to indicate that down-converted frequency $\omega_s$ of down-converted signal 129 is lower frequency than the fundamental frequency ω of fundamental laser signal 128. In a specific embodiment, down-converted frequency $\omega_s$ is also higher than 50% (½) of fundamental frequency ω (i.e., $0.5\omega < \omega_s < \omega$). OPA 119 is configured to mix down-converted seed signal 118 with fundamental light portion 127 to generate down-converted signal 129 at the required (second) peak power level (i.e., greater than ten times the first peak power level). One advantage of generating higher power down-converted signal 129 by mixing lower power down-converted seed signal 118 with fundamental light is that it is much easier to control the stability and bandwidth of lower powered laser light, so generating down-converted seed signal 118 at the lower (first) peak power level facilitates greater control over down-converted frequency $\omega_s$ of down-converted signal 129. Another advantage of generating higher power down-converted signal 129 using lower power down-converted seed signal 118 is that this approach facilitates generating down-converted signal 129 by way of passing down-converted seed signal 118 and fundamental frequency portion 127 through OPA 119 only once, which (as explained in additional detail below) minimizes distortion of down-converted signal 129 caused by idler frequencies when higher power down-converted signals are used to generate 183 nm laser output light 140.

The functional arrangement and operation of each of the core components mentioned above is described in additional detail below with reference to the detailed description of laser assembly 100A (FIG. 1A). Unless otherwise specified, the additional details provided below with reference to FIG. 1A apply to the corresponding core components used in laser assembly 100B, and thus repeating the additional detail is omitted from the description of FIG. 1B (below) for the sake of brevity.

Referring to FIG. 1A, in addition to the core components mentioned above, laser assembly 100A utilizes a beam splitter 120 that is optically coupled between fundamental laser 102 and both OPS 116 and fifth harmonic generator 103. Specifically, fundamental laser 102 generates fundamental light 128 that is directed onto beam splitter 120, which functions to divide fundamental light 128 into two portions: a first portion 127 that is directed in a first (e.g., downward) direction to OPS 116, and a second portion 130 that is directed in a second (e.g., horizontal) direction to fifth harmonic generator 103. OPS 116 down-converts fundamental light portion 127 using OPA 119 and transmits down-converted signal 129 having down-converted frequency $\omega_s$ to frequency mixing module 104. Fifth harmonic generator module 103 converts fundamental light portion 130 and transmits fifth harmonic light 134 to frequency mixing module 104. Frequency mixing module 104 mixes down-converted signal 129 and fifth harmonic light 134 to generate laser output light 140.

Referring to the left portion of FIG. 1A, fundamental laser 102 is configured using known techniques to generate fundamental light 128 (referred to simply as the "fundamental" in the industry) at fundamental frequencies within a fundamental bandwidth (range) Δω. In one embodiment, fundamental laser 102 is configured such that fundamental light 128 is generated at a fundamental frequency ω corresponding to an infra-red wavelength approximately 1064 nm. In an exemplary embodiment, fundamental laser 102 is implemented using one of a Nd:YAG (neodymium-doped yttrium aluminum garnet) lasing medium, a Nd-doped yttrium orthovanadate lasing medium, or by an ytterbium-doped fiber laser. Suitable fundamental lasers are commercially available as pulsed (Q-switched, mode-locked or quasi-CW) from Coherent Inc. (including models in the Paladin family with repetition rates of 80 MHz and 120 MHz), Newport Corporation (including models in the Explorer family) and other manufacturers. Laser power levels for such fundamental lasers can range from milliWatts to tens of Watts or more. In an alternate exemplary embodiment, fundamental laser 102 is implemented by a laser using a Nd:YLF (neodymium-doped yttrium lithium fluoride) lasing medium that generates fundamental laser light at a fundamental wavelength near 1053 nm or 1047 nm. In yet another exemplary embodiment, fundamental laser 102 can be implemented by an ytterbium-doped fiber laser that generates fundamental laser light at a fundamental wavelength near 1030 nm.

Referring to the right of fundamental laser 102 in FIG. 1A, beam splitter 120 functions to divide fundamental light 128 into fundamental light portions 127 and 130 that are respectively directed to OPS 116 and fifth harmonic generator module 103. In a preferred embodiment, beam splitter 120 comprises an etalon or other wavelength selective device that selects first and second portions from the fundamental wavelength such that the second portion 130 comprises a narrower range of wavelengths within the fundamental wavelength bandwidth than the first portion 127. Using a wavelength selective device for beam splitter 120 allows the output bandwidth of the laser to be controlled independently of the bandwidth of fundamental laser 102. Further details of how a wavelength selective device may be used to control the output bandwidth of a deep UV laser, such as laser generating a wavelength near 183 nm, can be found in U.S. patent application Ser. No. 14/300,227 filed on Jun. 9, 2014 by Deng et al. This patent application is incorporated by reference herein. In one embodiment, 183 nm laser assembly 100A is configured to operate at repetitions rates higher than 1 MHz, which is important for high-speed inspection applications. To achieve this high repetition rate operation, fundamental laser 102 is implemented using a mode-locked or quasi-CW fundamental laser operating at a repetition rate greater than or about 50 MHz, which is particularly advantageous for high-speed inspection of semiconductor wafers, photomasks, and reticles because the use of such high repetition rates allows high-speed image acquisition and reduces the peak power of each pulse (and so causes less damage to the optics and to the article being inspected) compared with a lower repetition rate laser of the same power. Although the present invention is described herein using various fundamental wavelengths that facilitate generating laser output light 140 at the desired 183 nm wavelength, other wavelengths within a few nanometers of 183 nm can be generated using different fundamental wavelengths (i.e., when mixed with an appropriate signal frequency). Unless otherwise specified in the appended claims, such lasers and systems utilizing such lasers are considered within the scope of this invention.

OPS 116, which is located below beam splitter 120 in FIG. 1A, is configured to receive and down-convert first portion 127 of fundamental light 128 such that this down-conversion generates a down-converted signal 129 at the required down-converted frequency $\omega_s$ (i.e., such that mixing down-converted signal 129 and fifth harmonic light 134 produces output laser light 140 at approximately 183 nm). In alternative embodiments, OPS 116 includes an optical parametric oscillator (GPO), an optical parametric amplifier (OPA), or a combination of both an OPO and an OPA.

According to an aspect of the present invention, OPS 116 also includes a wavelength selective device 117, such as a volume Bragg grating or a narrow-band, stabilized seed diode, that operates in conjunction with the OPO or OPA to determine the frequency $\omega_s$ and bandwidth of down-converted signal 129, where the specific wavelength selective utilized in a given specific embodiment is selected based on the frequency/wavelength of fundamental light 128 and the desired wavelength of laser output light 140. For example, when fundamental laser 102 generates fundamental light 128 at a wavelength approximately 1064 nm (such as a wavelength between about 1064 nm and about 1065 nm), then wavelength selective device 117 is implemented by a specific wavelength selective device that causes OPS 116 to generate down-converted signal 129 at a frequency corresponding to a wavelength of between about 1250 nm and about 1420 nm such that, when mixed with fifth harmonic light 134 generated by fifth harmonic generation module 103 based on the 1064 nm fundamental frequency, causes laser assembly 100A to generate laser output light 140 at a wavelength between about 182 nm and about 185 nm. In another example, when fundamental laser 102 generates fundamental light 128 at a wavelength of approximately 1053 nm (i.e., such as a wavelength between about 1053 nm and about 1054 nm), then wavelength selective device 117 is implemented by another specific wavelength selective device that causes OPS 116 to generate down-converted signal 129 at a frequency corresponding to a wavelength of between about 1290 nm and about 1520 nm so as to generate laser output light 140 at a wavelength between about 181 nm and about 185 nm. In yet another example, when fundamental laser 102 generates fundamental light 128 at a wavelength of approximately 1047 nm (i.e., such as a wavelength between about 1047 nm and about 1048 nm), then wavelength selective device 117 is implemented by yet another specific wavelength selective device that causes OPS 116 to generate down-converted signal 129 at a frequency corresponding to a wavelength of between about 1290 nm and about 1580 nm so as to generate laser output light 140 at a wavelength between about 180 nm and about 185 nm. In a final example, when fundamental laser 102 generates fundamental light 128 at a wavelength of approximately 1030 nm (i.e., such as a wavelength between about 1029 nm and about 1031 nm), then wavelength selective device 117 is implemented by yet another specific wavelength selective device that causes OPS 116 to generate down-converted signal 129 at a frequency corresponding to a wavelength of between about 1400 nm and about 1830 nm so as to generate a laser output light 140 at a wavelength between about 179 nm and about 185 nm. Given these exemplary values, those skilled in the art will understand how to select a proper wavelength selective device for a given fundamental frequency and laser output wavelength.

Referring again to FIG. 1A, second portion 130 of fundamental light 128 is directed from beam splitter 120 towards fifth harmonic generation module 103, which is configured and functions to generate fifth harmonic light 134 having a frequency that is five time the fundamental frequency $\omega$ by way of converting fundamental portion 130. If the bandwidth of second fundamental portion 130 is narrower than the bandwidth of fundamental light 128 (i.e., because beam splitter 120 comprises a wavelength selective device), then fifth harmonic light 134 will also have a narrower bandwidth than if it had been generated directly from fundamental light 128 without using a wavelength selective device.

Figure 2:
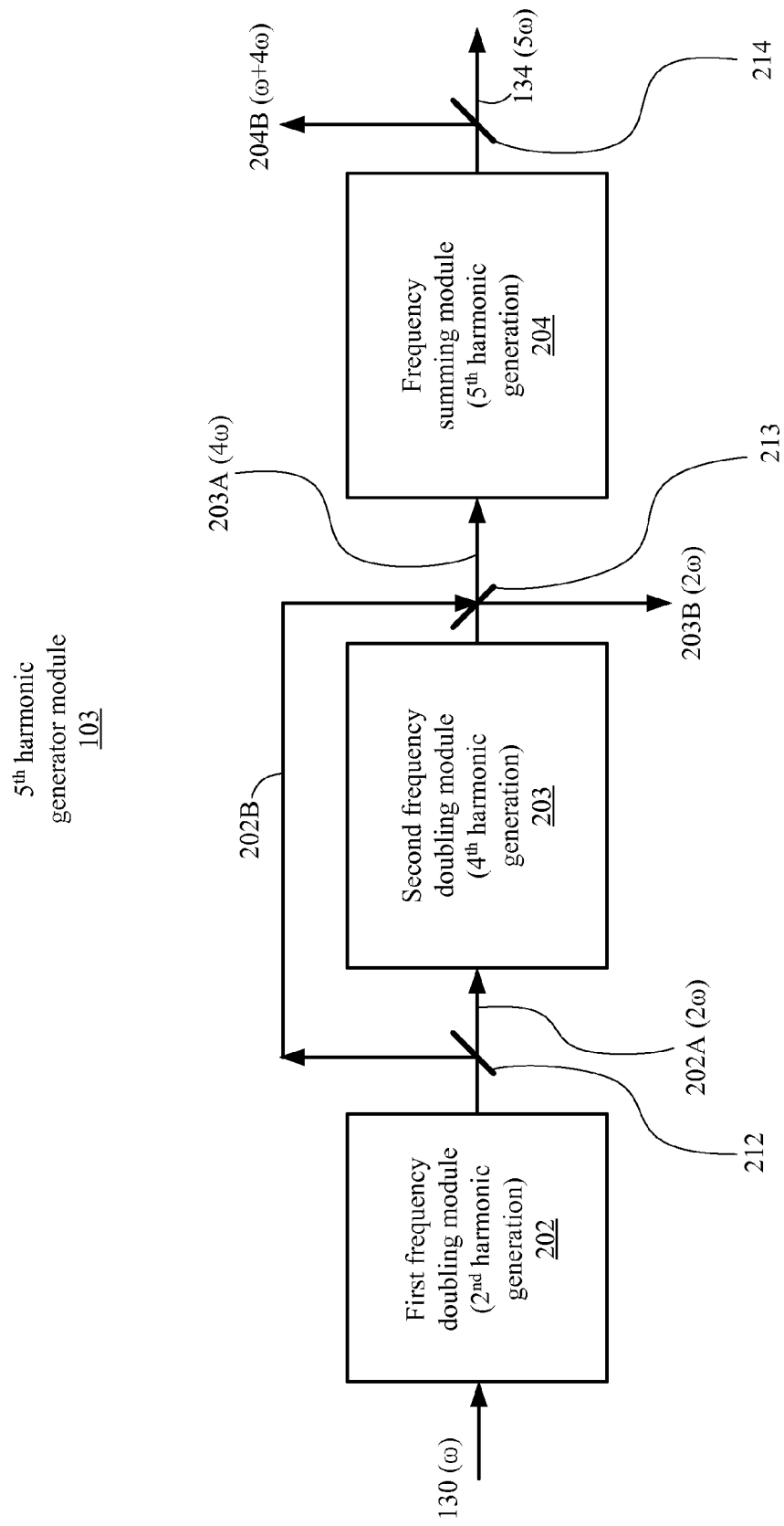
FIG. 2 is a simplified block diagram showing an exemplary fifth harmonic generator utilized in the 183 nm laser assemblies of FIG. 1A according to an embodiment of the present invention.

FIG. 2 shows fifth harmonic generator module 103 including a first frequency doubling module ($2^{nd}$ harmonic generation) 202, an optional beam splitter/prism 212, a second frequency doubling module ($4^{th}$ harmonic generation) 203, an optional beam splitter/combiner 213, a frequency summing module ($5^{th}$ harmonic generation) 204, and an optional beam splitter or wavelength separator 214 according to a presently preferred embodiment. In general, fifth harmonic generator module 103 functions to generate fifth harmonic light 134 by way of utilizing frequency doubling modules 202 and 203 to convert a portion of the input signal at fundamental frequency $\omega$ (i.e., second fundamental portion 130) to generate fourth harmonic laser light 203A at four times the fundamental frequency ($4\omega$), and then utilizes frequency summing module 204 to mix fourth harmonic laser light 203A with an unconsumed portion of the input light. According to a presently preferred embodiment, at least one of first frequency doubling module 202, second frequency doubling module 203, and frequency summing module 204 is implemented using an annealed CLBO crystal, a deuterium-treated CLBO crystal or a hydrogen-treated CLBO crystal.

Fifth harmonic generator module 103 generates fourth harmonic laser light 203A by generating second harmonic laser light 202A by way of first frequency doubling module 202, and then doubling second harmonic laser light 202A using second frequency doubling module 203. Referring to the left side of FIG. 2, first frequency doubling module 202 receives and converts fundamental portion 130 at fundamental frequency $\omega$ to form second harmonic light 202A at two times the fundamental frequency ($2\omega$). Second frequency doubling module 203 receives and converts second harmonic light 202A to form fourth harmonic light 203A at four times the fundamental frequency ($4\omega$). An unconsumed portion 202B of fundamental light 130 exiting first frequency doubling module 202 may be separated out from second harmonic light 202A by a beam splitter or prism 212 and directed towards frequency summing module 204. In one embodiment (not shown), unconsumed fundamental portion 202B is not separated from the second harmonic 202A and co-propagates with second harmonic light 202A through second frequency doubling module 203 to arrive at frequency summing module 204 substantially coincident with fourth harmonic 203A. One advantage of separating unconsumed fundamental portion 202B from second harmonic light 202A is that an appropriate time delay can be applied either to unconsumed fundamental portion 202B or to fourth harmonic light 203A so that the two laser pulses arrive at frequency summing module 204 at substantially the same time. A further advantage is that optical elements such as mirrors, lens and prisms (not shown) used for directing and/or focusing the light can be separately optimized in each path for the appropriate wavelength.

In one embodiment, unconsumed second harmonic portion 203B (i.e., a portion of the second harmonic light not used within second frequency doubling module 203) is separated from the fourth harmonic 203A by optional beam splitter/combiner 213. Beam splitter/combiner 213 may comprise one or more beam splitters and/or one or more prisms. Beam splitter/combiner 213 may, if needed, combine unconsumed fundamental 202B with fourth harmonic 203A so that they propagate together to frequency summing module 204.

Referring to the right side of FIG. 2, frequency summing module 204 generates fifth harmonic light 134 by summing the fourth harmonic light 203A with unconsumed fundamental light portion 202B. Optional beam splitter or wavelength separator 214 is utilized in some embodiments to separate out any unconsumed fundamental and fourth harmonic 204B from fifth harmonic light 134. Beam splitter 214 may comprise a prism, a polarizing beam splitter, a dichroic beam splitter or a combination of optical elements.

In one preferred embodiment, second harmonic generation module 202 comprises a lithium triborate (LBO) crystal for frequency conversion. In other embodiments, second harmonic generation module 202 comprises a CLBO, BBO, or other non-linear crystal for frequency conversion. In one preferred embodiment of fifth harmonic generator 103, fourth harmonic generation module 203 comprises a CLBO crystal for frequency conversion. In other embodiments, fourth harmonic generation module 203 may comprise a BBO or other non-linear crystal for frequency conversion. In one preferred embodiment of fifth harmonic generator 103, frequency summing module 203 comprises a CLBO crystal for frequency summing. In other embodiments, frequency summing module 204 may comprise a BBO or other non-linear crystal for frequency summing.

FIG. 3 shows a table of exemplary wavelength ranges (in nm) for the 183 nm laser shown in FIG. 1. For each fundamental laser type, an exemplary short-wavelength fundamental and an exemplary long-wavelength fundamental are shown, along with the wavelengths corresponding to the harmonics and the down-converted signal required for the desired output wavelength (183 nm in the example shown in the table). The exact wavelength of a fundamental laser depends on many factors including the exact composition of the lasing medium, the operating temperature of the lasing medium, and the design of the optical cavity. Two lasers using the same laser line of a given lasing medium may operate at wavelengths that differ by a few tenths of 1 nm or a few nm due to the aforementioned and other factors. One skilled in the appropriate arts would understand how to choose the appropriate wavelength for the down-converted signal in order to generate the desired output wavelength from any fundamental wavelength close to those listed in the table. Similarly, if the desired output wavelength differs from 183 nm by a few nm, the desired output wavelength can also be achieved by an appropriate adjustment of the wavelength for the down-converted signal.

Figure 4:
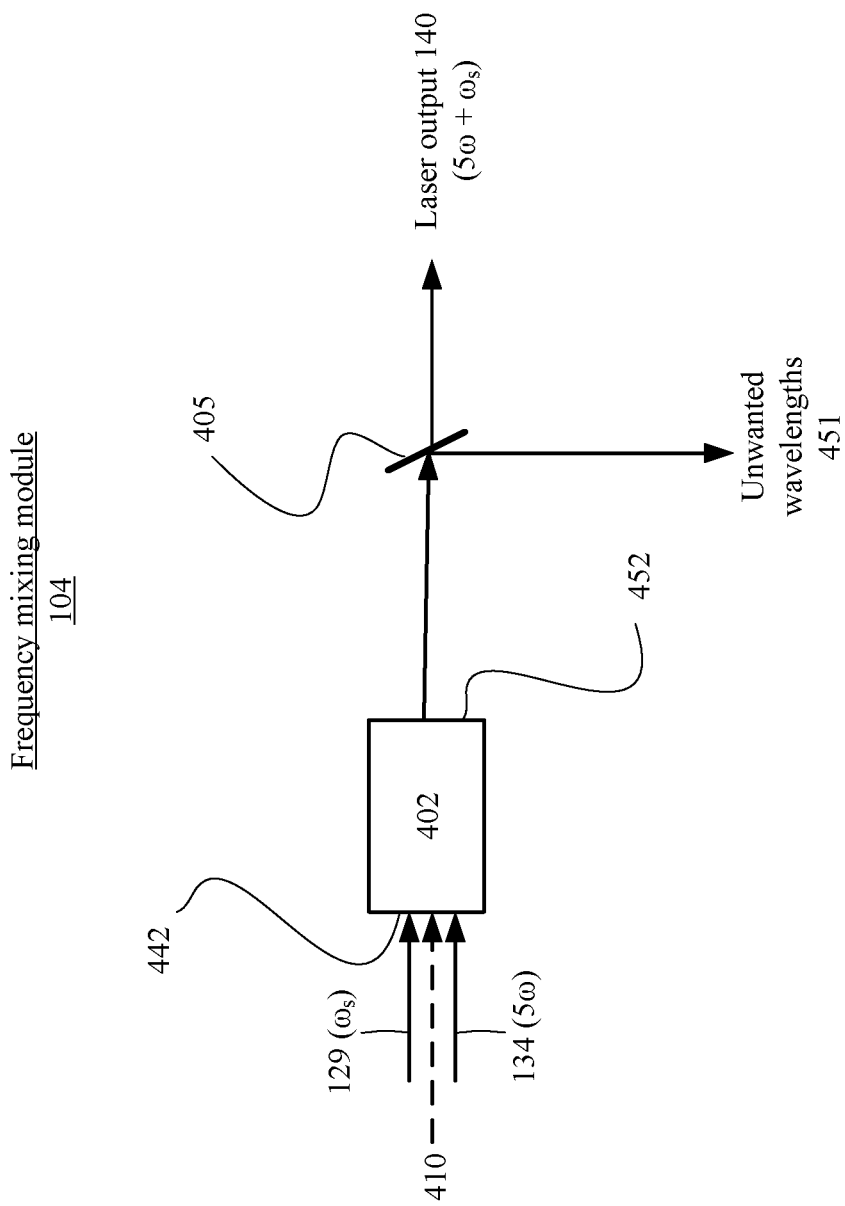
FIG. 4 is a simplified block diagram showing an exemplary frequency mixing module utilized in the 183 nm laser assemblies of FIG. 1A according to an embodiment of the present invention.

FIG. 4 shows frequency mixing module 104 according to a preferred embodiment for use in laser assembly 100A (FIG. 1A). Frequency mixing module 104 includes a non-linear crystal 402, which in the preferred embodiment comprises an annealed (deuterium-treated or hydrogen-treated) cesium lithium borate (CLBO) crystal including an input surface 442 and an opposing output surface 452. Non-linear crystal 402 is positioned to receive at input surface 442 both fifth harmonic light 134 (i.e., from fifth harmonic generator 103) and down-converted signal 129 (from OPS generator 116) such that both signal 129 and light 134 enter non-linear crystal 402 approximately collinearly (e.g., in direction 410, indicated by dashed line arrow in FIG. 4), and are focused to corresponding beam waists disposed inside or proximate to crystal 402 (beam waists not shown). For type-I matching in CLBO at a temperature of approximately 50° C. with a down-converted signal having a wavelength near 1433 nm and a fifth harmonic having a wavelength near 206 nm, the phase-matching angle is approximately 74.9°. For type-I matching in CLBO at a temperature of approximately 50° C. with a down-converted signal having wavelength near 1274 nm and a fifth harmonic having a wavelength near 213 nm, the phase-matching angle is approximately 85.7°. Both of these example show that nearly non-critical phase matching with high efficiency and low walk-off can be achieved for generating wavelengths near 183 nm. These wavelength combinations are merely examples and are not meant to limit the scope of the invention. One skilled in the appropriate arts understands how to choose different combinations of wavelengths, temperature and angle to achieve phase matching.

In some embodiments, input surface 442 of crystal 402 is cut and positioned so as to be approximately at Brewster's angle relative to fifth harmonic light 134 (i.e., relative to direction 410 and the polarization of fifth harmonic light 134). This angle minimizes reflection of the fifth harmonic wavelength, and thus facilitates avoiding the need for an anti-reflection coating on input surface 442 in some embodiments. In other embodiments, an anti-reflection coating (not shown) is applied to surface 442 to reduce the reflected light at the fifth harmonic and/or the signal wavelengths. Output surface 452 of the crystal 402 may be coated or uncoated. In one embodiment output surface 452 of crystal 402 is cut and maintained at Brewster's angle relative to laser output light 140, and is not coated. Note that if type I phase matching is used, the polarization of laser output light 140 is preferably perpendicular to the polarization of the input wavelengths (i.e., of fifth harmonic light 134 and down-converted signal 129), and so the Brewster-angle output surface 452 must be cut appropriately. The advantage of not coating output surface 452 is that coatings can have a short lifetime when exposed to intense UV radiation.

Referring again to FIG. 4, in preferred embodiments frequency mixing module 104 may use one or more optical elements (optics) 405 to separate the desired output wavelength, i.e., the laser output light 140 at approximately 183 nm, from the other unwanted wavelengths 451 (e.g., unconsumed portions of fifth harmonic light 134 and/or unconsumed portions of down-converted signal 129). Optics 405 may include a beam splitter, a prism, a grating, or other optical elements. In some embodiments, the combination of walk-off and the angle of output surface 452 of crystal 402 may achieve sufficient separation of the laser output 140 from the other wavelengths such that optics 405 are not required.

In preferred embodiments of the 183 nm laser, a substantial fraction, or almost all, of fifth harmonic light 134 is consumed in the crystal 402 due to the use of a high power down-converted signal 129. Although this may result in lower overall conversion efficiency from fundamental light 128 (in FIG. 1) to laser output light 140, a laser that uses more power at the signal wavelength and less power at the fifth harmonic for a given output power can have a longer life and may require less frequent service because deep UV light, such as the fourth and fifth harmonics can easily cause damage and photocontamination to optics within the laser.

Note that, in any of the embodiments, mirrors, prisms, periscopes etc. may be used to direct the fundamental or other wavelengths as needed. Prisms, beam splitters, beam combiners and dichroic-coated mirrors, for example, may be used to separate and combine beams as necessary. Various combinations of mirrors and beam splitters may be used to separate and route the various wavelengths between the different frequency conversion stages in any appropriate sequence. The faces of frequency conversion crystals, prisms, beam splitters or lenses may be cut at an angle approximately equal to Brewster's angle for an incident wavelength in order to minimize or control reflection without using an anti-reflection coating. This cutting can be particularly advantageous for those surfaces where UV radiation is incident, because anti-reflection coatings may degrade when exposed to UV and thus may degrade the reliability of the laser if used on such surfaces. Waveplates (including Brewster-angle waveplates or retarders) or other optical elements may be used to rotate the polarization of any of the wavelengths as needed to align the polarization with the appropriate crystal axis of the next frequency conversion or frequency mixing stage. The use of Brewster angle optics in DUV lasers is described in more detail in U.S. Pat. No. 8,711,470 entitled "High Damage Threshold Frequency Conversion System" to Armstrong. This patent is incorporated by reference herein.

The above description and associated figures illustrate various lasers for generating light having a wavelength of approximately 183 nm. Some specific wavelengths and wavelength ranges are described in order to illustrate embodiments. Other laser embodiments similar to those described above that generate a different wavelength a few nm shorter or longer than 183 nm are possible and are within the scope of this invention.

The above-described figures are not meant to represent the actual physical layout of the components. The above-described figures show the main optical modules involved in the process, but do not show every optical element. One skilled in the appropriate arts would understand how to build the 183 nm laser from the above-described figures and their associated descriptions. It is to be understood that more or fewer optical components may be used to direct the light where needed. Lenses and/or curved mirrors may be used to focus the beam waist to foci of substantially circular or elliptical cross sections inside or proximate to the non-linear crystals where appropriate. Prisms, beam-splitters, gratings or diffractive optical elements may be used to steer or separate the different wavelengths at the outputs of each frequency convertor or mixer module when needed. Prisms, coated mirrors, or other elements may be used to combine the different wavelengths at the inputs to the frequency convertors and mixers as appropriate. Beam splitters or coated mirrors may be used as appropriate to divide one wavelength into two beams. Filters may be used to block or separate undesired wavelengths at the output of any stage. Waveplates may be used to rotate the polarization as needed. Other optical elements may be used as appropriate. In some cases, it may be acceptable to allow unconsumed light from one frequency conversion stage to pass to the next stage even though that light is not needed in the subsequent stage. This may be acceptable if the power density is low enough not to cause damage and if there is little interference with the desired frequency conversion process (for example because of no phase matching at the crystal angle or due to the polarization of the light). One skilled in the appropriate arts would understand the various tradeoffs and alternatives that are possible in the implementation of the 183 nm laser.

In a preferred embodiment, the first frequency doubling module 202 (FIG. 2) that generates the second harmonic can include a Lithium triborate (LBO) crystal, which can be substantially non-critically phase-matched (for the appropriate choice of crystal plane) at temperatures between room temperature and about 200° C. for producing a second harmonic in a wavelength range between about 515 nm and about 532 nm. In other embodiments, the first frequency doubling module 202 may include a Cesium Lithium Borate (CLBO) crystal or a beta-Barium Borate (BBO) crystal, either of which can be critically phase matched for generating a second harmonic in a wavelength range between about 515 nm and about 532 nm.

The second frequency doubling module 203 (FIG. 2) that generates the fourth harmonic and the frequency summing module 204 that generates the fifth harmonic may use critical phase matching in CLBO, BBO or other non-linear crystal. In preferred embodiments, both frequency doubling module 203 and frequency summing module 204 comprise CLBO crystals.

Any of the frequency conversion stages (including those shown in FIGS. 1A, 2 and 4) may advantageously use some, or all, of the methods and systems disclosed in U.S. Pat. No. 8,873,596, entitled "Laser With High Quality, Stable Output Beam, And Long Life High Conversion Efficiency Non-Linear Crystal" by Dribinski et al. This patent is incorporated by reference herein.

Any of the frequency conversion stages (including those shown in FIGS. 1A, 2 and 4) may include one or more protective environments, such as those described in U.S. Pat. No. 8,298,335, entitled "Enclosure for controlling the environment of optical crystals", by Armstrong. This patent is incorporated by reference herein. Note that a single protective environment may enclose multiple stages or a single stage.

Any of the frequency conversion stages (including those shown in FIGS. 1A, 2 and 4) may incorporate any of the methods or systems described in U.S. Pat. No. 8,298,335, entitled "Alleviation of laser-induced damage in optical materials by suppression of transient color centers formation and control of phonon population", to Dribinski et al., any of the apparatus or methods described in U.S. Pat. No. 8,824,514, entitled "Measuring crystal site lifetime in a non-linear optical crystal", by Armstrong, any of the apparatus and methods described in U.S. Pat. No. 8,976,343, entitled "Laser crystal degradation compensation" by Genis, any of the systems and methods described in U.S. Provisional Patent Application 61/837,053 entitled "Preferential shift direction to prolong the life and minimize perturbations of a scanning nonlinear optical crystal" and filed by Genis on Jun. 19, 2013, and any of the systems and methods described in U.S. Provisional Patent Applications 61/666,675 and 61/762,269, both entitled "Scan rate for continuous motion of a crystal in a frequency converted laser" and filed by Armstrong et al. on Jun. 29, 2012 and Feb. 7, 2013 respectively. The laser may further incorporate any of the systems and methods described in U.S. Pat. No. 8,686,331 entitled "Dynamic wavefront control of a frequency converted laser system" to Armstrong. All of these patents, applications and provisional applications are incorporated by reference herein.

Further note that any of the frequency conversion stages (including those shown in FIGS. 1A, 2 and 4) may advantageously use deuterium, hydrogen and/or fluorine doped or treated non-linear crystals. Such crystals may be created, processed or treated by any of the processes or methods described in U.S. Pat. No. 9,023,152 filed on Sep. 3, 2010 by Dribinski et al., or described in co-pending U.S. patent application Ser. No. 13/488,635 filed on Jun. 1, 2012 by Chuang et al., and Ser. No. 14/248,045 filed on Apr. 8, 2014 by Dribinski et al. These patents and applications are incorporated by reference herein. The doped or treated crystals may be particularly useful in those stages involving deep UV wavelengths, including the frequency doubling module 203, the frequency summing module 204, and the frequency mixing module 104.

Figure 5:
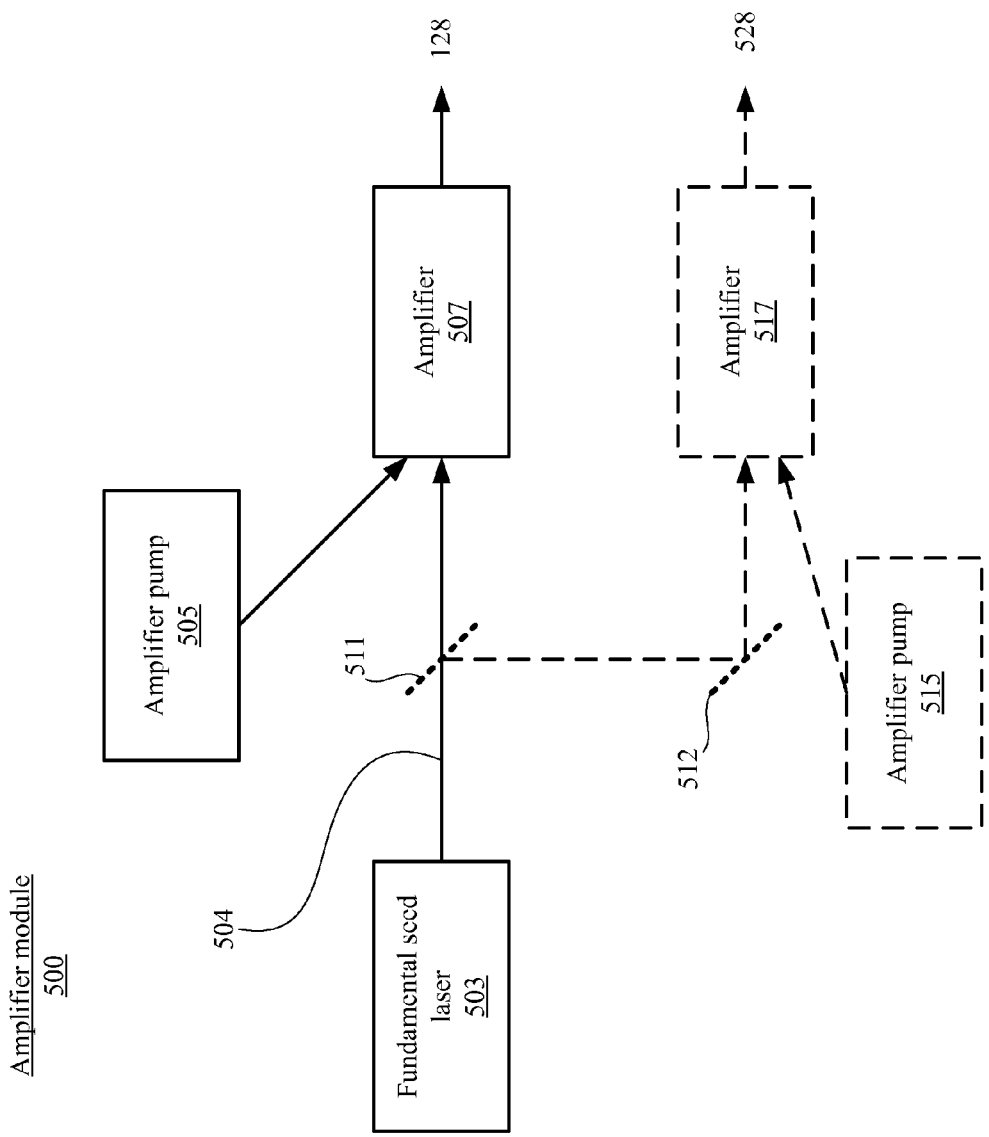
FIG. 5 is a simplified block diagram showing an amplifier module optionally utilized in the 183 nm laser assemblies of FIG. 1A to increase fundamental laser light power according to an embodiment of the present invention.

In some embodiments, in order to generate sufficient power at the fundamental wavelength, one or more amplifiers may be used to increase the power of the fundamental. If two or more amplifiers are used, then one seed laser should preferably be used to seed all the amplifiers so that they all output synchronized laser pulses at the same wavelength. FIG. 5 illustrates an exemplary amplifier module 500 in which a seed laser 503 can generate stabilized, narrow-band seed laser light 504 at the desired fundamental wavelength (e.g. approximately 1064 nm, approximately 1053 nm, approximately 1047 nm or approximately 1030 nm). In some embodiments, the seed laser 503 is one of a Nd-doped YAG laser, a Nd-doped yttrium orthovanadate laser, a Nd-doped YLF laser, a fiber laser, or a stabilized diode laser. The seed light 504 goes to a first amplifier 507 that amplifies the light to a higher power level to generate fundamental 128. In one embodiment, the first amplifier 507 comprises Nd-doped YAG or Nd-doped yttrium orthovanadate. In one embodiment, an amplifier pump 505 includes a laser that can pump the first amplifier 507. In some embodiments, this pumping can be done using one or more diode lasers operating at approximately 808 nm in wavelength or at approximately 888 nm in wavelength. In other embodiments, the first amplifier 507 may comprise an Yb-doped fiber amplifier.

FIG. 5 also illustrates exemplary additional components that may be used in some embodiments of the amplifier module 500. Because the OPO/OPA 116, the first frequency doubling module 202, and the frequency summing module 204 (FIGS. 1 and 2) receive the fundamental laser wavelength as an input, and depending on the output power required near 183 nm in wavelength, more fundamental laser light may be required that can be conveniently generated in a single amplifier at the required bandwidth, stability and beam quality. Indeed, increasing the power output of an optical amplifier can lead to increased bandwidth, degradation in the beam quality due to thermal lensing or other effects, reduced stability, and/or shortened lifetime.

Therefore, in some embodiments of the amplifier module 500, the first amplifier 507 and an additional second amplifier 517 can be used to respectively generate two fundamental laser outputs 128 and 528, where fundamental light 128 is utilized as mentioned above, and light 528 can be directed to different frequency conversion stages (not shown) in place of, for example, 127 (in FIG. 1A) or 202B (in FIG. 2). The second amplifier 517 can be substantially identical to the first amplifier 507. In one embodiment, an amplifier pump 515 includes a laser that can pump the second amplifier 517. The amplifier pump 515 can be substantially identical to the amplifier pump 505. Notably, the same seed laser 503 can be used to seed both lasers in order to ensure that the outputs 128 and 528 are at the same wavelength and are synchronized. A beam splitter or prism 511 and a mirror or prism 512 can divide the seed light 504 and direct a fraction of it to the second amplifier 517.

Figure 6A:
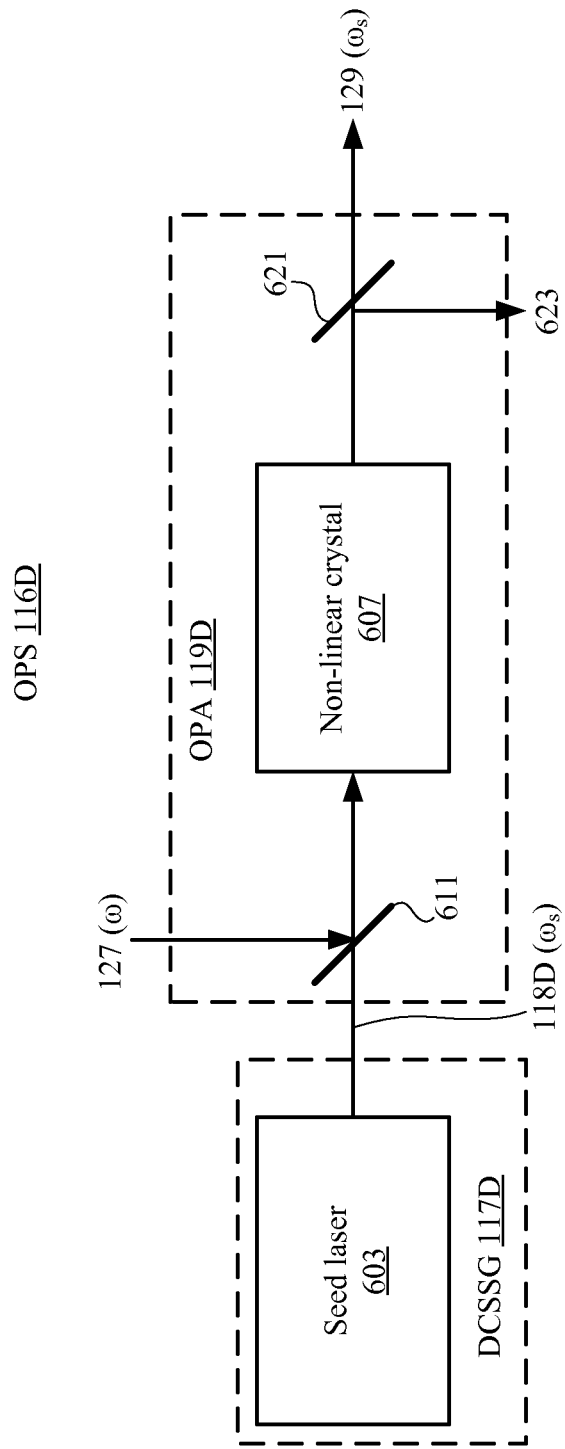
FIGS. 6A and 6B are simplified block diagrams showing exemplary optical parametric systems configured to generate the down-converted signal utilized in the 183 nm laser assemblies of FIG. 1A according to alternative specific embodiments of the present invention.
Figure 6B:
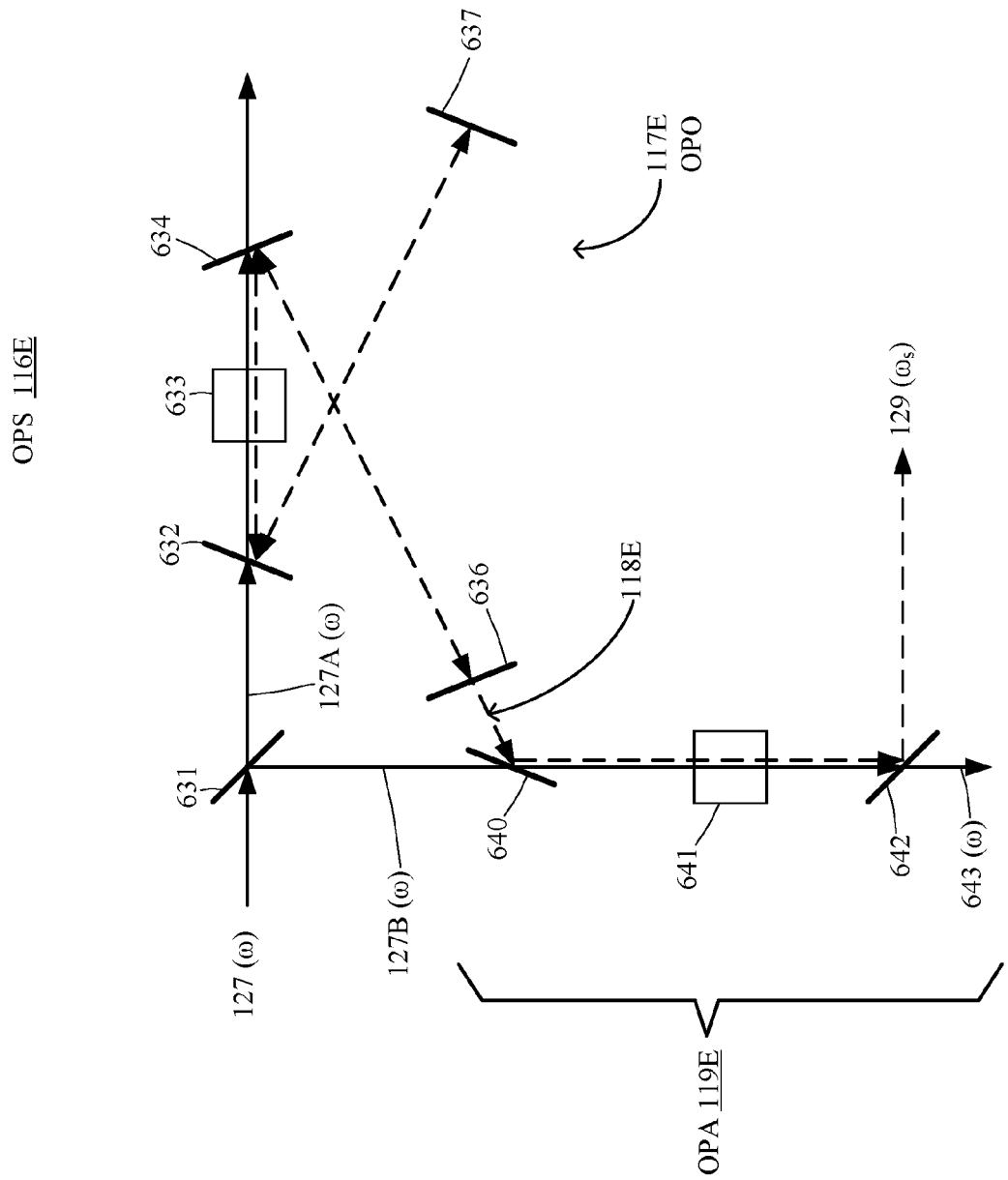

FIGS. 6A and 6B respectively show an OPS 116D and an OPS 116E according to two alternative exemplary embodiments. As mentioned above with reference to FIG. 1A, OPS 116 includes a down-converted signal seed generator (DC-SSG) 117 that generates a lower power down-converted seed signal 118 that is then combined with fundamental light portion 127 using an optical parametric amplifier (OPA) 119 to generate higher power down-converted signal 129, which is then transmitted to frequency mixing module 104 for mixing with fifth harmonic light 134. As set forth in the following exemplary embodiments, OPS 116D and OPS 116E utilize similar OPA structures, but utilize two different DCSSG arrangements. Specifically, where OPS 116D (FIG. 6A) utilizes a seed laser to directly generate the down-converted seed signal, OPS 116E (FIG. 6B) utilizes an optical parametric oscillator to generate the down-converted seed signal by converting a portion of the fundamental laser light. Advantages of each of these approaches are set forth in the following descriptions.

Referring to FIG. 6A, OPS 116D generally includes a down-converted signal seed generator (DCSSG) 117D, which is implemented using a seed laser 603, and OPA 119D including a beam combiner 611, a non-linear crystal 607, and a beam splitter 621. Seed laser 603 is configured to directly generate down-converted seed light 118D at the desired down-converted signal frequency $\omega_s$, and to direct down-converted seed light 118D onto beam combiner 611 in OPA 119D. Beam combiner 611 is configured and positioned to receive both fundamental light portion 127 (input laser light) at fundamental frequency $\omega$ with down-converted seed light 118D, and to combine (i.e., to direct along collinear paths) both fundamental light portion 127 and down-converted seed light 118D such that they enter non-linear crystal 607. Non-linear crystal 607 is configured to amplify down-converted seed signal 118 by stimulated down-conversion of fundamental light portion 127, and to transmit the amplified signal toward beam splitter (wavelength separator) 621. Beam splitter 621 is configured to separate down-converted signal 129 from other frequencies present in the amplified signal received from non-linear crystal 607, and to direct down-converted signal 129 to the frequency mixing module (not shown). Each of these components is described in additional detail in the following paragraphs.

In a preferred embodiment, the seed laser 603 is implemented using a diode laser or a low-powered fiber laser, and configured to generate the seed laser light 604 at down-converted signal frequency $\omega_s$, which is then used to seed the down conversion process at that frequency. The seed laser 603 need only be of approximately 1 mW to a few hundred mW in average power. In a preferred embodiment, the seed laser 603 is stabilized by using, for example, a grating and stabilizing the temperature. The seed laser frequency and bandwidth determine the frequency and bandwidth of the down-converted signal 129. An advantage of using a seed laser is that it is much easier to control the stability and bandwidth of lower powered laser than a high powered laser. A stable, narrow bandwidth seed laser determines the bandwidth and stability of the down-converted signal 129. In one embodiment, seed laser 603 generates polarized light that is then introduced into non-linear converter 607 polarized substantially perpendicular to the polarization of the fundamental, i.e. the input laser light 127.

In one embodiment, beam combiner 611 (e.g., a prism) includes a dichroic coating that efficiently reflects a first wavelength while transmitting a second wavelength such that fundamental light portion 127 and transmitted seed laser light 118D travel substantially collinearly through non-linear converter 607. For example, as indicated in FIG. 6A, beam combiner 611 reflects fundamental light portion 127 and transmits seed laser light 118D such that both are transmitted substantially collinearly through non-linear converter 607, as shown. In an alternative embodiment (not shown), the beam combiner is configured and arranged to transmit the fundamental light portion and to reflect the seed laser light such that both travel substantially collinearly through the non-linear converter.

In one embodiment, non-linear crystal 607 is implemented using any suitable non-linear optical crystal or periodically poled non-linear optical crystal that can phase match, or quasi-phase match, for the input laser frequency $\omega$ and the down-converted signal frequency $\omega_s$. In one preferred embodiment, non-linear crystal 607 comprises one of periodically polled lithium niobate, periodically polled magnesium-oxide doped lithium niobate, periodically polled stoichiometric lithium tantalate (PPSLT), periodically polled magnesium-oxide doped stoichiometric lithium tantalate, and periodically polled potassium titanyl phosphate (PP-KTP).

In one embodiment, beam splitter 621 (e.g., a prism) is configured and positioned using known techniques to separate the down-converted signal 129 from unwanted frequencies 623 (e.g., unconsumed fundamental and an idler). In one embodiment (not shown), the unconsumed fundamental may be recirculated back to the input of non-linear converter 607 with a time delay set to match the next incoming laser pulse of fundamental light portion 127.

FIG. 6B illustrates an OPS 116E according to a second exemplary embodiment that generates high power down-converted signal 129 (such as more than about 3 W) at the required down-converted signal frequency $\omega_s$ by way of converting a portion of the fundamental laser light. OPS 116E generally includes a beam splitter 631 configured to split fundamental light portion 127 at fundamental frequency $\omega$ into a first sub-portion 127A and a second sub-portion 127B, an optical parametric oscillator (OPO; i.e., down-converted seed signal generator) 117E configured to generate down-converted seed signal 118E by way of converting fundamental light sub-portion 127A, and an OPA 119E configured to mix down-converted seed signal 118E with (second) fundamental light sub-portion 127B. OPO 117E includes a first focusing mirror 632, a non-linear crystal 633, a second focusing mirror 634, a wavelength selector 637, and an output coupler 636 that are operably configured as shown to form an optical cavity in which light is reflected between wavelength selector 637 and output coupler 636 by way of focusing mirrors 632 and 634 and non-linear crystal 633. Similar to the OPA of OPS 116D (FIG. 6A), OPA 119E includes a beam combiner 640, a non-linear crystal 641 and wavelength separator 642. Each of these components is described in additional detail in the following paragraphs.

Referring to the left side of FIG. 6B, in one embodiment fundamental light portion (input laser light) 127 at fundamental frequency $\omega$ is divided by beam splitter 631 such that sub-portion 127A directed to OPO 117E includes less than 50% of the energy of input laser light 127, and sub-portion 127B directed to OPA 119E includes more than 50% of the energy of input laser light 127. Sub-portion 127A enters OPO 117E by way of passing through focusing mirror 632. Focusing or mode matching optics (not shown) may be placed in the light path of input laser light 127 before OPO 117E to focus sub-portion 127A near the center of non-linear crystal 633.

Non-linear crystal 633 is designed for phase matching or quasi-phase matching for producing light at the signal frequency $\omega_s$ from sub-portion 127A at frequency $\omega$. In one embodiment, non-linear crystal 633 comprises a periodically poled material such as periodically polled lithium niobate (PPLN) or periodically polled stoichiometric lithium tantalate (PPSLT). Any input laser light not converted to signal frequency light by non-linear crystal 633 passes through focusing mirror 634 and may be dumped. Focusing mirror 634 should preferably also transmit the idler frequency that is created in non-linear crystal 633.

In one embodiment, focusing mirror 634 is configured to be highly reflective for light at the signal frequency $\omega_s$, and arranged to direct light at the signal frequency created in, or passing through, non-linear crystal 633 to output coupler 636. Output coupler 636 transmits a first fraction of the light incident on it at the signal frequency $\omega_s$ (such as a fraction of approximately 20%) and reflects a second fraction of the light (such as approximately 80%). The second fraction of the light at signal frequency $\omega_s$ is reflected back to focusing mirror 634, which redirects the light through non-linear crystal 633 to focusing mirror 632, which in turn redirects the light to wavelength selector 637.

Wavelength selector 637 is configured using known techniques to be highly reflective for a narrow range of frequencies centered on the desired signal frequency $\omega_s$. For example, wavelength selector 637 may reflect a wavelength range of approximately 0.2 nm FWHM. Wavelength selector 637 is important for determining the wavelength of the laser output 140 (see, e.g., FIG. 1a) since the wavelength of the laser output 140 is the wavelength corresponding to the sum of the fifth harmonic of the fundamental and the signal frequency $\omega_s$. In one embodiment wavelength selector 637 comprises a volume Bragg grating. In a preferred embodiment, wavelength selector 637 is held at a constant temperature in order to ensure that its center wavelength remains constant. In one embodiment, small adjustments to the wavelength of the laser output 140 can be made by adjusting the temperature of wavelength selector 637 in order to change the signal frequency $\omega_s$.

Down-converted light at the signal frequency $\omega_s$, after reflection from wavelength selector 637, returns to focusing mirror 632, which directs it back to non-linear crystal 633. The optical path length followed by light at the signal frequency $\omega_s$ from non-linear crystal 633 to focusing mirror 634 to output coupler 636, back to focusing mirror 634 through non-linear crystal 633 to focusing mirror 632, to wavelength selector 637, back to focusing mirror 632, and back to non-linear crystal 633 should be such that each pulse of light at signal frequency $\omega_s$ arrives back at non-linear crystal 633 substantially simultaneously with a pulse of input laser light 127. This arrangement is used to ensure that pulses of the input laser light 127 and light at the signal frequency substantially co-propagate through the non-linear crystal 633 to enable stimulated down-conversion of input laser light to light at the signal frequency $\omega_s$. In a preferred embodiment the optical path length should be such that the mismatch in the arrival times of pulses of light at the signal frequency $\omega_s$ with pulses of the input laser light 127 is less than about 10% of a width of a pulse of the input laser light 127.

In one embodiment, focusing mirrors 632 and 634 are configured to include focal lengths set such that pulses of light at the signal frequency arrive back at non-linear crystal 633, after the complete round trip just described, focused near the center of non-linear crystal and substantially spatially overlapped with pulses of the input laser light 127. In alternative embodiments, wavelength selector 637 and/or output coupler 636 may focus light at the signal frequency $\omega_s$ instead of, or in addition to, focusing mirrors 632 and 634. In another embodiment, one or more lenses may be used to refocus the signal frequency instead of, or in addition to, focusing mirrors.

Note also that the relative locations of output coupler 636 and wavelength selector 637 could be swapped, as long as appropriate layout changes are made to incorporate additional mirrors and/or prisms to redirect light at the signal frequency $\omega_s$ and the second portion of the input laser light 127B to beam combiner 640. The layout shown in FIG. 6B is intended to be illustrative to explain the principles of operation.

Other OPO configurations known in the art may be substituted for OPO 117E. For example, a ring cavity OPO or bow-tie cavity OPO may be used. Other modifications may be made to OPO 117E without departing from the scope of the present invention. For example, a mirror may be used in place of wavelength selector 637, and a transmissive wavelength selector (not shown) could be included in the optical path of the signal frequency $\omega_s$. Additional flat mirrors or prisms may be included in OPO 117E to, for example, achieve the desired optical path length while maintaining a compact overall size.

For high power laser output 140, such as a power of 1 W or more, it is preferred to generate the signal wavelength $\omega_s$ directly from the fundamental laser light rather than from the second harmonic of the fundamental, since less power is wasted and, therefore, a lower power fundamental laser 102 (e.g. FIG. 1A) may be used for a given output power. In general, an OPO may be able to generate a high average output power, such as power of a few Watts, or more, of signal frequency $\omega_s$ as would be needed to generate around 1 W or more of laser output 140. The present invention is directed towards generating a laser output 140 with a wavelength between about 180 nm and 185 nm from a fundamental wavelength near 1 μm. This requires a signal frequency $\omega_s$ corresponding to a wavelength between about 1.2 μm and about 1.6 μm (some example wavelength combinations are shown in FIG. 3). Generating such a short wavelength relative to the wavelength of the fundamental laser means that the idler created at the same time as the signal frequency must have a long wavelength, such as a wavelength longer than about 4 μm. Readily available, high gain, high quality non-linear crystals suitable for generating signal wavelengths between about 1.2 μm and about 1.6 μm from a wavelength near 1 μm, such as PPLN and PPSLT, are strongly absorbing at wavelengths longer than about 4 μm. If OPO 117E were used to generate high power at a signal frequency in the desired range, the idler would also contain significant power. Because of absorption of the idler by non-linear crystal 633, significant temperature gradients will be created within non-linear crystal 633 when the idler power is high. These temperature gradients locally change the optical properties of non-linear crystal 633, resulting in an irregular profile for the light generated at the signal frequency $\omega_s$, and, likely, unstable operation of OPO 117E.

In the present invention, these problems are overcome by operating OPO 117E so as to generate a relative low output power at the signal frequency $\omega$, such as an average power of a few hundred mW. At such an output power, local heating of non-linear crystal 633 is minimal and OPO 117E can operate stably with good profile for down-converted seed signal 118E. Non-linear crystal 633 may be chosen so as to maximize conversion efficiency, for example, by using a long length of a material with a high non-linear coefficient such as PPLN or PPSLT, with less concern for damage or thermal properties.

In the present invention, light at the signal frequency $\omega_s$ 118E generated by OPO 117E is amplified by OPA 119E to the required power level as down-converted signal 129. Beam combiner 640 combines the second portion of the input laser light 127 with light at the signal frequency $\omega_s$ from OPO 117E. The optical path length from beam splitter 631 to beam combiner 640 should be such that pulses of input laser light arrive at beam combiner 640 at substantially the same time as pulses of light at the signal frequency $\omega_s$. Additional mirrors, prisms or other optical components may be placed in the optical path between 631 and 640 and/or the optical path between 636 and 640, to ensure that pulses arrive at 640 substantially simultaneously. Lenses, curved mirrors or other optical elements (not shown) may be used in either light path as required to ensure that the second portion of input laser light 127 and the light at the signal frequency $\omega_s$ are substantially spatially overlapped and both focused near the center of non-linear crystal 641.

Beam combiner 640 directs light pulses to non-linear crystal 641. Non-linear crystal 641 amplifies light at the signal frequency $\omega_s$ by stimulated down-conversion of second fundamental light sub-portion 127B. Wavelength separator 642 separates the down-converted signal 129 from any unconsumed input laser light 643 and any idler. Wavelength separator 642 may comprise a polarized beam splitter (if the down-converted signal 129 has a different polarization from the input laser light), a dichroic mirror, a Pellin-Broca prism or any other appropriate wavelength separator known in the art. Non-linear crystal 641 may comprise any suitable non-linear optical crystal or periodically poled non-linear optical crystal that can phase match, or quasi-phase match, for the input laser frequency $\omega$ and the down-converted signal frequency $\omega_s$. In one preferred embodiment, non-linear crystal 641 comprises PPSLT or periodically poled Mg-doped SLT. These materials are particularly suited for operation at higher power levels.

Because the down-converted signal 129 passes only once through non-linear crystal 641, the thermal gradients in crystal 641 cause less degradation of the profile of the light than would be caused in an OPO configured to generate a similar output power. That is, if OPA 119E were replaced with an OPO (e.g., configured such as OPO 117E), light at the signal frequency $\omega_s$ would be required to pass multiple times through its non-linear crystal (e.g., non-linear crystal 633 in OPO 117E), resulting in significant heating by the idler. Thus, by utilizing the two-step approach of first generating a lower power seed signal and then mixing the seed signal with a portion of the fundamental light to generate down-converted signal 129 at the required frequency and power level, the present invention overcomes a significant limitation of using just an OPO to generate a high power down-converted signal 129.

Referring to FIG. 1B, as mentioned above, laser assembly 100B is similar to laser assembly 100A (FIG. 1A) in that both laser assemblies includes a fundamental laser 102 configured to generate fundamental light 128 having a fundamental wavelength co, an OPS 116 optically coupled to receive a portion 127 of fundamental light 128 and to generate a down-converted signal 129, a fifth harmonic module 157, and a frequency mixing module 104 configured to receive and mix down-converted signal 129 and fifth harmonic laser light 134 from fifth harmonic generator 157 in order to generate laser output light 140. In addition, OPS 116 generates down-converted signal 129 by way of utilizing DCSSG 117 to generate lower power down-converted seed signal 118 at down-converted wavelength $\omega_s$, and then mixing down-converted seed signal 118 with fundamental light portion 127.

A first difference between laser assembly 100B and laser assembly 100A (FIG. 1A) is that the entirety of fundamental light 128 generated by fundamental laser 102 is transmitted to a second harmonic generation module 153, and portions 127 and 130 supplied to OPS 116 and fifth harmonic module 157 are obtained from unused fundamental light 182 exiting second harmonic generation module 153. This approach illustrates a beneficial alternative for cases in which fundamental laser 102 outputs second fundamental light and unused fundamental light (i.e., where fundamental laser effectively includes second harmonic generation module 153). To facilitate this alternative, a first beam splitter 181 is utilized to separate second harmonic light 189 exiting second harmonic generation module 102 from unused fundamental light 182 such that second harmonic light 189 is transmitted to a fourth harmonic generation module 155, and such that unused fundamental light 182 is transmitted to a second beam splitter 183 that generates portions 127 and 130 that are respectively directed to OPS 116 and fifth harmonic module 157.

Aside from the differences mentioned above, the operation of laser assembly 100B is essentially the same as that of laser assembly 100A. Second harmonic generation module 153 functions substantially similarly to, and may be configured similarly to, first frequency doubling module 202 (FIG. 2). Fourth harmonic generation module 155 functions substantially similarly to, and may be configured similarly to, second frequency doubling module 203 (FIG. 2). Fifth harmonic generation module 157 functions substantially similarly to, and may be configured similarly to, frequency summing module 204 (FIG. 2). In other words, modules 153, 155 and 157 perform substantially the same function as fifth harmonic generation module 103, but with a different routing of the fundamental between the various modules.

FIGS. 7-12 illustrate systems that can include one of the above-described 183 nm lasers. These systems can be used in photomask, reticle, or wafer inspection and metrology applications.

Figure 7:
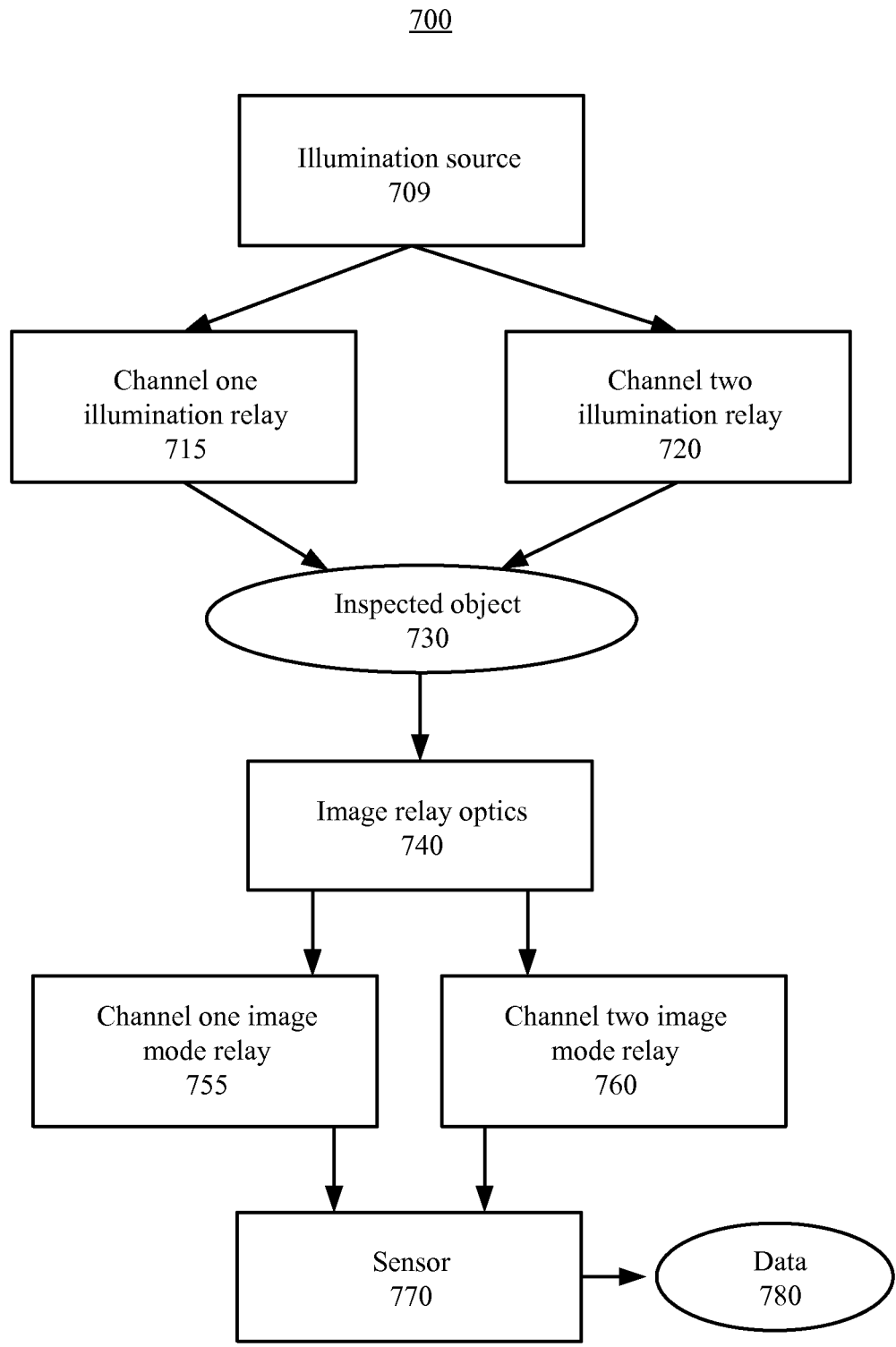
FIG. 7 shows a reticle, photomask, or wafer inspection system that simultaneously detects two channels of image or signal on one sensor.

FIG. 7 shows a reticle, photomask, or wafer inspection system 700 that simultaneously detects two channels of image or signal using a single sensor 770. The illumination source (laser assembly) 709 is configured to generate laser output light 710 having an output wavelength in the range of approximately 180 nm to approximately 185 nm (e.g., 183 nm) as described herein. Illumination source 709 may further comprise a pulse repetition-rate multiplier and/or a coherence reducing scheme. The two image/signal channels may comprise reflected and transmitted light when an inspected object, which is disposed on a stage 730, is transparent (for example a reticle or photomask), or may comprise two different illumination modes, such as angles of incidence, polarization states, wavelength ranges or some combination thereof.

As shown in FIG. 7, inspection system 700 includes illumination relay (first) optics 715 and 720, which are optical systems configured using known techniques to relay the illumination (laser output light) 710 from source 709 to the object being inspected, which is disposed on stage 730. The inspected object may be a reticle, a photomask, a semiconductor wafer or other article to be inspected. Inspection system 700 also includes image relay (second) optics 740, 755, and 760, which are optical systems configured using known techniques to relay a portion 710' of illumination 710 that is affected by (i.e., reflected, scattered and/or transmitted from) the inspected object to a sensor 770. The data corresponding to the detected signals or images for the two channels is shown as data 780 and is transmitted to a computer (not shown) for processing.

Other details of a reticle or photomask inspection system that may be configured to measure transmitted and reflected light from the reticle or photomask are described in U.S. Pat. No. 5,563,702 to Emery et al., U.S. Pat. No. 7,352,457 to Kvamme et al., and U.S. Pat. No. 7,528,943 to Brown et al., which are incorporated by reference herein.

Figure 8:
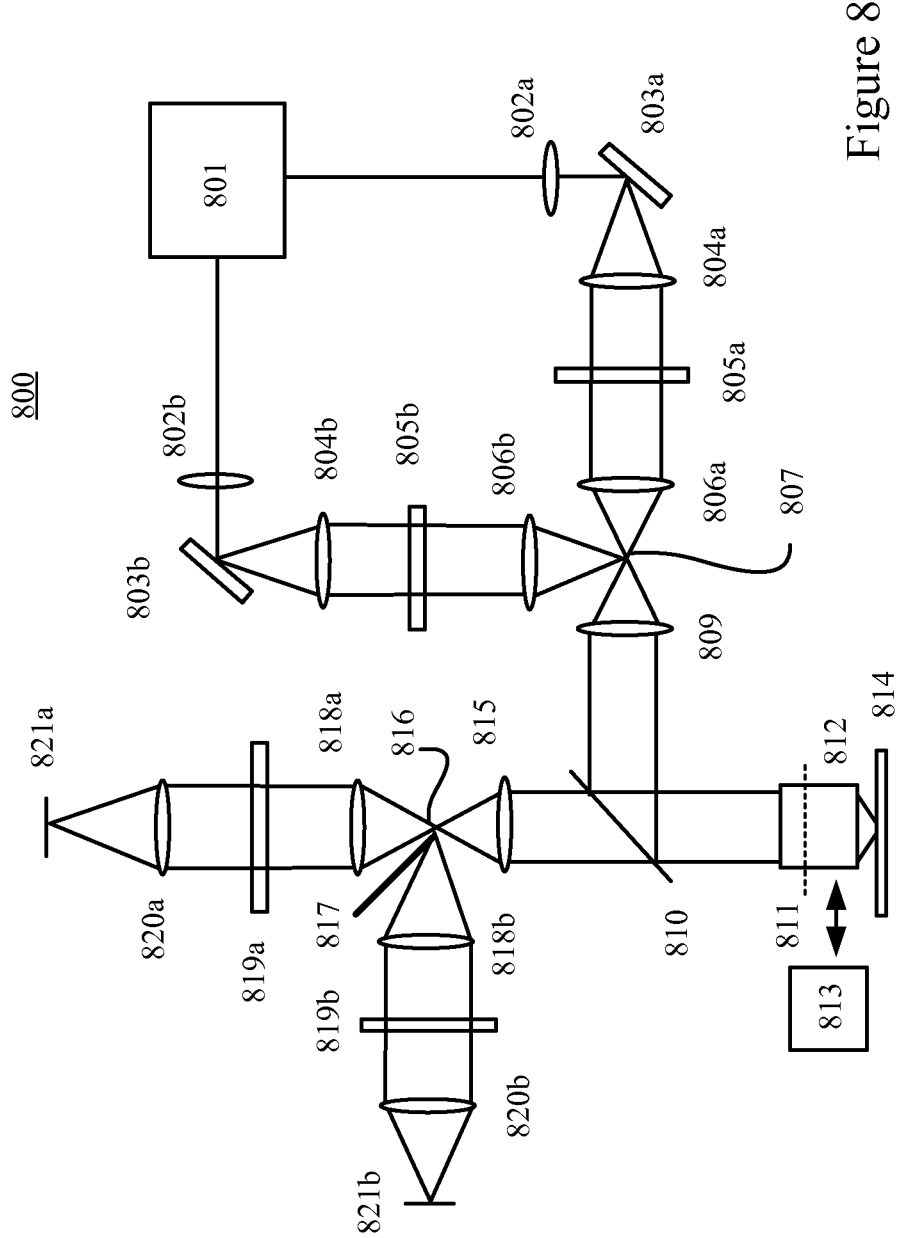
FIG. 8 illustrates an exemplary inspection system including multiple objectives and one of the above-described improved 193 nm lasers.

FIG. 8 illustrates an exemplary inspection system 800 including multiple objectives and one of the above-described 183 nm laser assemblies. In system 800, illumination from a laser source 801 is sent to multiple sections of the illumination subsystem. A first section of the illumination subsystem includes elements 802a through 806a. Lens 802a focuses light from laser source 801. Light from lens 802a then reflects from mirror 803a. Mirror 803a is placed at this location for the purposes of illustration, and may be positioned elsewhere. Light from mirror 803a is then collected by lens 804a, which forms illumination pupil plane 805a. An aperture, filter, or other device to modify the light may be placed in pupil plane 805a depending on the requirements of the inspection mode. Light from pupil plane 805a then passes through lens 806a and forms illumination field plane 807.

A second section of the illumination subsystem includes elements 802b through 806b. Lens 802b focuses light from laser source 801. Light from lens 802b then reflects from mirror 803b. Light from mirror 803b is then collected by lens 804b which forms illumination pupil plane 805b. An aperture, filter, or other device to modify the light may be placed in pupil plane 805b depending on the requirements of the inspection mode. Light from pupil plane 805b then passes through lens 806b and forms illumination field plane 807. The light from the second section is then redirected by mirror or reflective surface such that the illumination field light energy at illumination field plane 807 is comprised of the combined illumination sections.

Field plane light is then collected by lens 809 before reflecting off a beamsplitter 810. Lenses 806a and 809 form an image of first illumination pupil plane 805a at objective pupil plane 811. Likewise, lenses 806b and 809 form an image of second illumination pupil plane 805b at objective pupil plane 811. An objective 812 (or alternatively 813) then takes the pupil light and forms an image of illumination field 807 at sample 814. Objective 812 or objective 813 can be positioned in proximity to sample 814. Sample 814 can move on a stage (not shown), which positions the sample in the desired location. Light reflected and scattered from the sample 814 is collected by the high NA catadioptric objective 812 or objective 813. After forming a reflected light pupil at objective pupil plane 811, light energy passes through beamsplitter 810 and lens 815 before forming an internal field 816 in the imaging subsystem. This internal imaging field is an image of sample 814 and correspondingly illumination field 807. This field may be spatially separated into multiple fields corresponding to the illumination fields. Each of these fields can support a separate imaging mode. For example, one imaging mode may be a bright-field imaging mode, while another may be a dark-field imaging mode.

One of these fields can be redirected using mirror 817. The redirected light then passes through lens 818b before forming another imaging pupil 819b. This imaging pupil is an image of pupil 811 and correspondingly illumination pupil 805b. An aperture, filter, or other device to modify the light may be placed in pupil plane 819b depending on the requirements of the inspection mode. Light from pupil plane 819b then passes through lens 820b and forms an image on sensor 821b. In a similar manner, light passing by mirror or reflective surface 817 is collected by lens 818a and forms imaging pupil 819a. Light from imaging pupil 819a is then collected by lens 820a before forming an image on detector 821a. Light imaged on detector 821a can be used for a different imaging mode from the light imaged on sensor 821b.

The illumination subsystem employed in system 800 is composed of laser source 801, collection optics 802-804, beam shaping components placed in proximity to a pupil plane 805, and relay optics 806 and 809. An internal field plane 807 is located between lenses 806 and 809. In one preferred configuration, laser source 801 can include one of the above-described 183 nm lasers.

With respect to laser source 801, while illustrated as a single uniform block having two points or angles of transmission, in reality this represents a laser source able to provide two channels of illumination, for example a first channel of light energy such as laser light energy at a first frequency (e.g. a deep UV wavelength near 183 nm) which passes through elements 802a-806a, and a second channel of light energy such as laser light energy at a second frequency (e.g. a different harmonic, such as the $4^{th}$ or $5^{th}$ harmonic, from the same laser, or a light from a different laser) which passes through elements 802b-806b.

While light energy from laser source 801 is shown to be emitted 90 degrees apart, and the elements 802a-806a and 802b-806b are oriented at 90 degree angles, in reality light may be emitted at various orientations, not necessarily in two dimensions, and the components may be oriented differently than as shown. FIG. 8 is therefore simply a representation of the components employed and the angles or distances shown are not to scale nor specifically required for the design.

Elements placed in proximity to pupil plane 805a/805b may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. Numerical aperture can be reduced to a desired value by using internal apertures placed at the pupil planes 805a, 805b, 819a, and 819b.

Multiple objectives may also be used as shown in FIG. 8. For example, although two objectives 812 and 813 are shown, any number is possible. Each objective in such a design may be optimized for each wavelength produced by laser source 801. These objectives 812 and 813 can either have fixed positions or be moved into position in proximity to the sample 814. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of this configuration may approach or exceed 0.97, but may in certain instances be smaller. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 815. The purpose of the image forming optics 815 is to form an internal image 816 of sample 814. At this internal image 816, a mirror 817 can be placed to redirect light corresponding to one of the inspection modes. It is possible to redirect the light at this location because the light for the imaging modes are spatially separate. The image forming optics 818 (818a and 818b) and 820 (820a and 820b) can be implemented in several different forms including a varifocal zoom, multiple afocal tube lenses with focusing optics, or multiple image forming mag tubes. U.S. Pat. No. 7,957,066, issued Jun. 7, 2011 and incorporated by reference herein, describes additional details regarding system 800.

Figure 9:
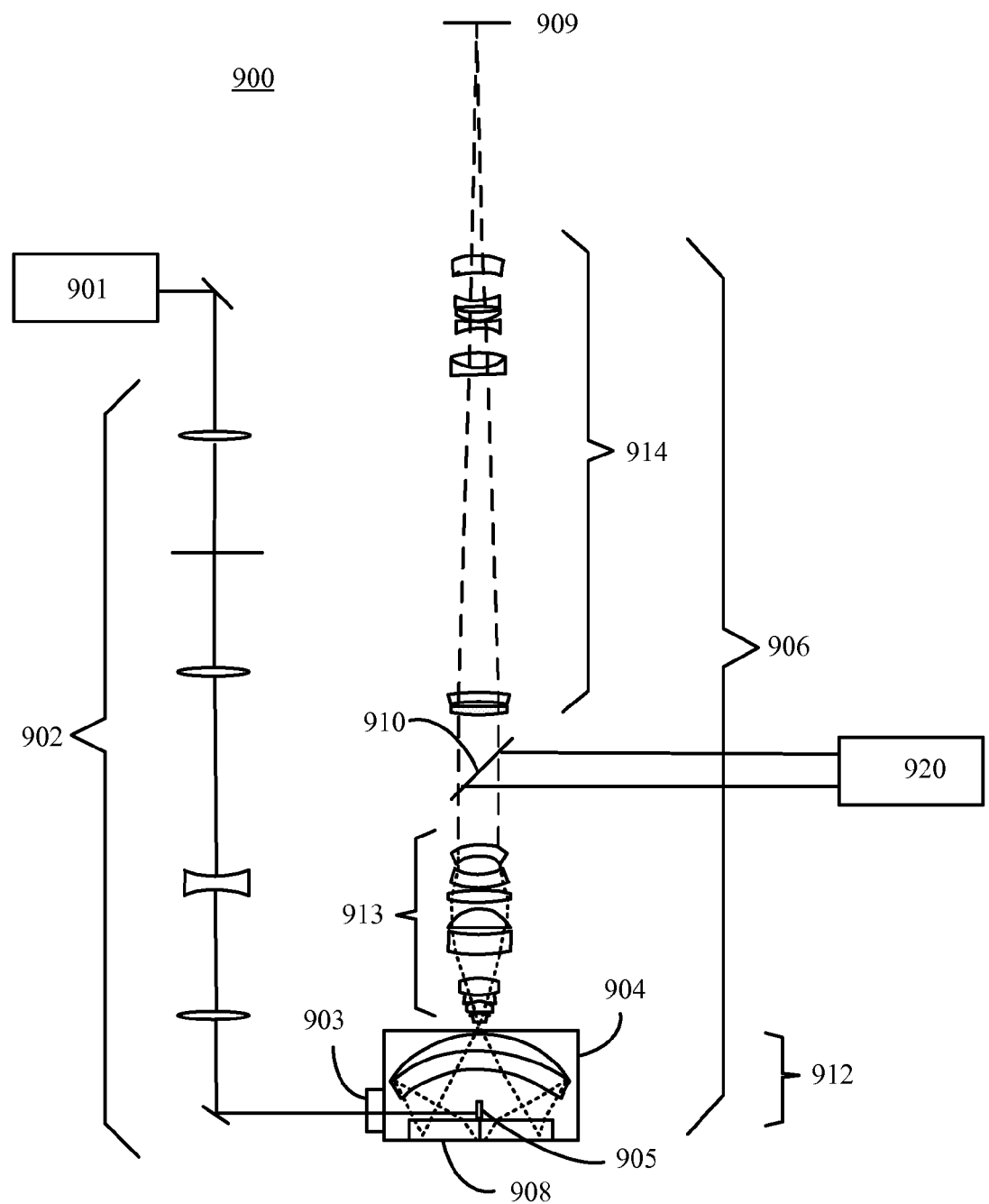
FIG. 9 illustrates the addition of a normal incidence laser dark-field illumination to a catadioptric imaging system.

FIG. 9 illustrates an exemplary catadioptric imaging system 900 configured as an inspection system with bright-field and dark-field inspection modes. System 900 may incorporate two illuminations sources: a laser 901, and a broad-band light illumination module 920. In one embodiment, laser 901 may include a 183 nm laser as described herein.

In a dark-field mode, light from laser 901 is directed to adaptation optics 902, which control the laser illumination beam size and profile on the surface being inspected. Mechanical housing 904 includes an aperture and window 903, and a prism 905 to redirect the laser along the optical axis at normal incidence to the surface of a sample 908. Prism 905 also directs the specular reflection from surface features of sample 908 out of objective 906. Objective 906 collects light scattered by sample 908 and focuses it on a sensor 909. Lenses for objective 906 can be provided in the general form of a catadioptric objective 912, a focusing lens group 913, and a tube lens section 914, which may, optionally, include a zoom capability.

In a bright-field mode, broad-band illumination module 920 directs broad-band light to beam splitter 910, which reflects that light towards focusing lens group 913 and catadioptric objective 912. Catadioptric objective 912 illuminates the sample 908 with the broadband light. Light that is reflected or scattered from sample 908 is collected by objective 906 and focused on sensor 909. Broad-band illumination module 920 comprises, for example, a laser-pumped plasma light source or an arc lamp. Broad-band illumination module 920 may also include an auto-focus system to provide a signal to control the height of sample 908 relative to catadioptric objective 912.

U.S. Pat. No. 7,345,825, entitled "Beam delivery system for laser dark-field illumination in a catadioptric optical system" to Chuang et al., U.S. Pat. No. 8,665,536 entitled "External beam delivery system for laser dark-field illumination in a catadioptric optical system" to Armstrong, and U.S. Pat. No. 8,896,917, entitled "External beam delivery system using catadioptric objective with aspheric surfaces" to Armstrong, all of which are incorporated by reference herein, describe system 900 in further detail.

Figure 10A:
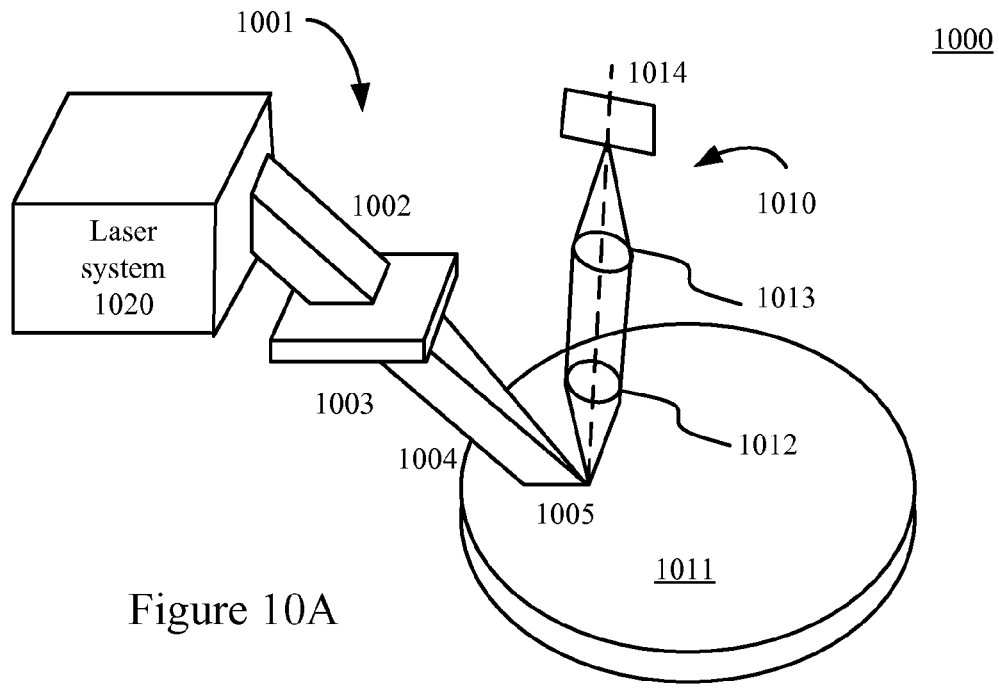
FIG. 10A illustrates a surface inspection apparatus that includes an illumination system and a collection system for inspecting areas of a surface.

FIG. 10A illustrates a surface inspection apparatus 1000 that includes illumination system 1001 and collection system 1010 for inspecting areas of surface 1011. As shown in FIG. 10A, a laser system 1020 directs a light beam 1002 through a lens 1003. In a preferred embodiment, laser system 1020 includes one of the above-described 183 nm lasers, an annealed crystal, and a housing to maintain the annealed condition of the crystal during standard operation by protecting it from moisture or other environmental contaminants. First beam shaping optics can be configured to receive a beam from the laser and focus the beam to an elliptical cross section at a beam waist in or proximate to the crystal.

Lens 1003 is oriented so that its principal plane is substantially parallel to a sample surface 1011 and, as a result, illumination line 1005 is formed on surface 1011 in the focal plane of lens 1003. In addition, light beam 1002 and focused beam 1004 are directed at a non-orthogonal angle of incidence to surface 1011. In particular, light beam 1002 and focused beam 1004 may be directed at an angle between about 1 degree and about 85 degrees from a normal direction to surface 1011. In this manner, illumination line 1005 is substantially in the plane of incidence of focused beam 1004.

Collection system 1010 includes lens 1012 for collecting light scattered from illumination line 1005 and lens 1013 for focusing the light coming out of lens 1012 onto a device, such as charge coupled device (CCD) 1014, comprising an array of light sensitive detectors. In one embodiment, CCD 1014 may include a linear array of detectors. In such cases, the linear array of detectors within CCD 1014 can be oriented parallel to illumination line 1015. In one embodiment, CCD 1014 may be an electron-bombarded CCD or a linear array of avalanche photo-detectors. In one embodiment, multiple collection systems can be included, wherein each of the collection systems includes similar components, but differ in orientation.

Figure 10B:
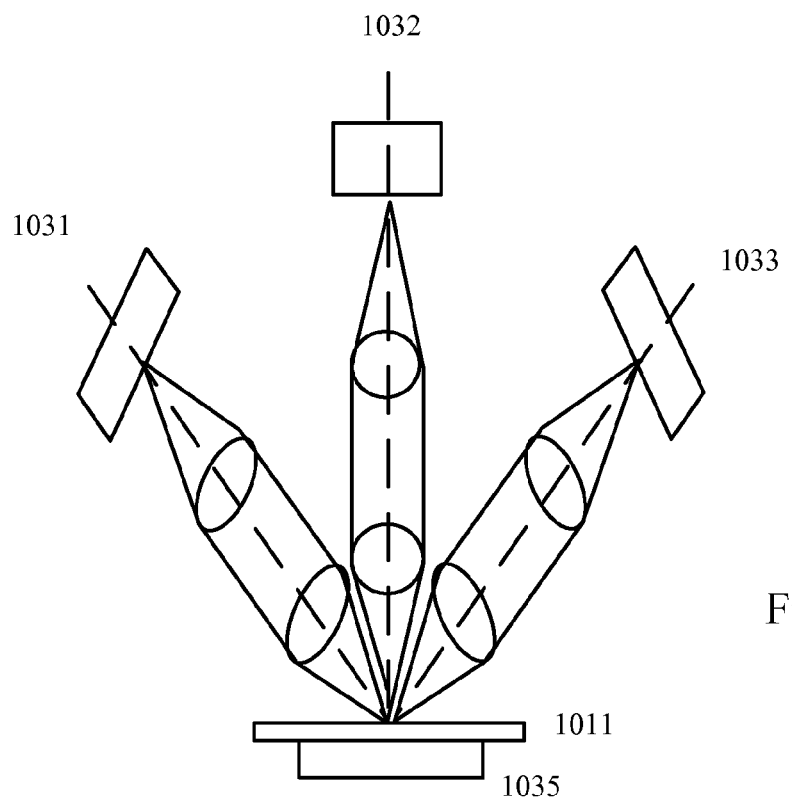
FIG. 10B illustrates an exemplary array of collection systems for a surface inspection apparatus.

For example, FIG. 10B illustrates an exemplary array of collection systems 1031, 1032, and 1033 for a surface inspection apparatus (wherein its illumination system, e.g. similar to that of illumination system 1001, is not shown for simplicity). First optics in collection system 1031 collect light scattered in a first direction from the surface of sample 1011. Second optics in collection system 1032 collect light scattered in a second direction from the surface of sample 1011. Third optics in collection system 1033 collect light scattered in a third direction from the surface of sample 1011. Note that the first, second, and third paths are at different angles of incidence to said surface of sample 1011. A platform 1035 supporting sample 1011 can be used to cause relative motion between the optics and sample 1011 so that the whole surface of sample 1011 can be scanned. U.S. Pat. No. 7,525,649, which issued to Leong et al. on Apr. 28, 2009 and is incorporated by reference herein, describes surface inspection apparatus 1000 and other multiple collection systems in further detail.

Figure 11:
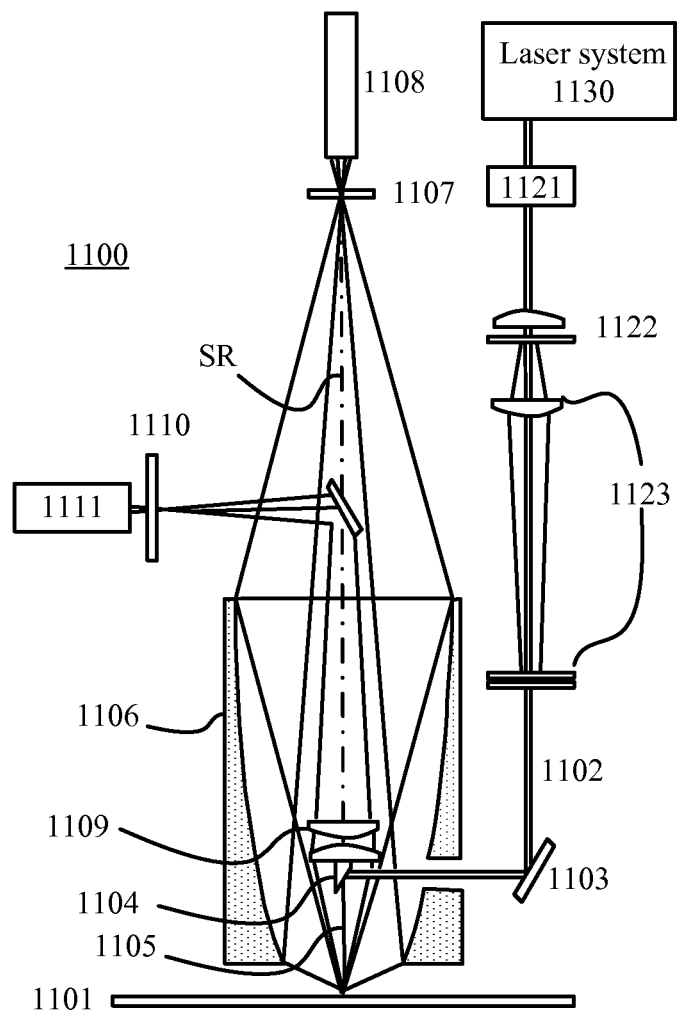
FIG. 11 illustrates a surface inspection system that can be used for inspecting anomalies on a surface.

FIG. 11 illustrates a surface inspection system 1100 that can be used for inspecting anomalies on a surface 1101. In this embodiment, surface 1101 can be illuminated by a substantially stationary illumination device portion of a laser system 1130 comprising one of the above-described 183 nm lasers. The output of laser system 1130 can be consecutively passed through polarizing optics 1121, a beam expander and aperture 1122, and beam-forming optics 1123 to expand and focus the beam.

The focused laser beam 1102 is then reflected by a beam folding component 1103 and a beam deflector 1104 to direct the beam 1105 towards surface 1101 for illuminating the surface. In the preferred embodiment, beam 1105 is substantially normal or perpendicular to surface 1101, although in other embodiments beam 1105 may be at an oblique angle to surface 1101.

In one embodiment, beam 1105 is substantially perpendicular or normal to surface 1101 and beam deflector 1104 reflects the specular reflection of the beam from surface 1101 towards beam turning component 1103, thereby acting as a shield to prevent the specular reflection from reaching the detectors. The direction of the specular reflection is along line SR, which is normal to the surface 1101 of the sample. In one embodiment where beam 1105 is normal to surface 1101, this line SR coincides with the direction of illuminating beam 1105, where this common reference line or direction is referred to herein as the axis of inspection system 1100. Where beam 1105 is at an oblique angle to surface 1101, the direction of specular reflection SR would not coincide with the incoming direction of beam 1105; in such instance, the line SR indicating the direction of the surface normal is referred to as the principal axis of the collection portion of inspection system 1100.

Light scattered by small particles are collected by mirror 1106 and directed towards aperture 1107 and detector 1108. Light scattered by large particles are collected by lenses 1109 and directed towards aperture 1110 and detector 1111. Note that some large particles will scatter light that is also collected and directed to detector 1108, and similarly some small particles will scatter light that is also collected and directed to detector 1111, but such light is of relatively low intensity compared to the intensity of scattered light the respective detector is designed to detect. In one embodiment, detector 1111 can include an array of light sensitive elements, wherein each light sensitive element of the array of light sensitive elements is configured to detect a corresponding portion of a magnified image of the illumination line. In one embodiment, inspection system can be configured for use in detecting defects on unpatterned wafers. U.S. Pat. No. 6,271,916, which issued to Marx et al. on Aug. 7, 2001 and is incorporated by reference herein, describes inspection system 1100 in further detail.

Figure 12:
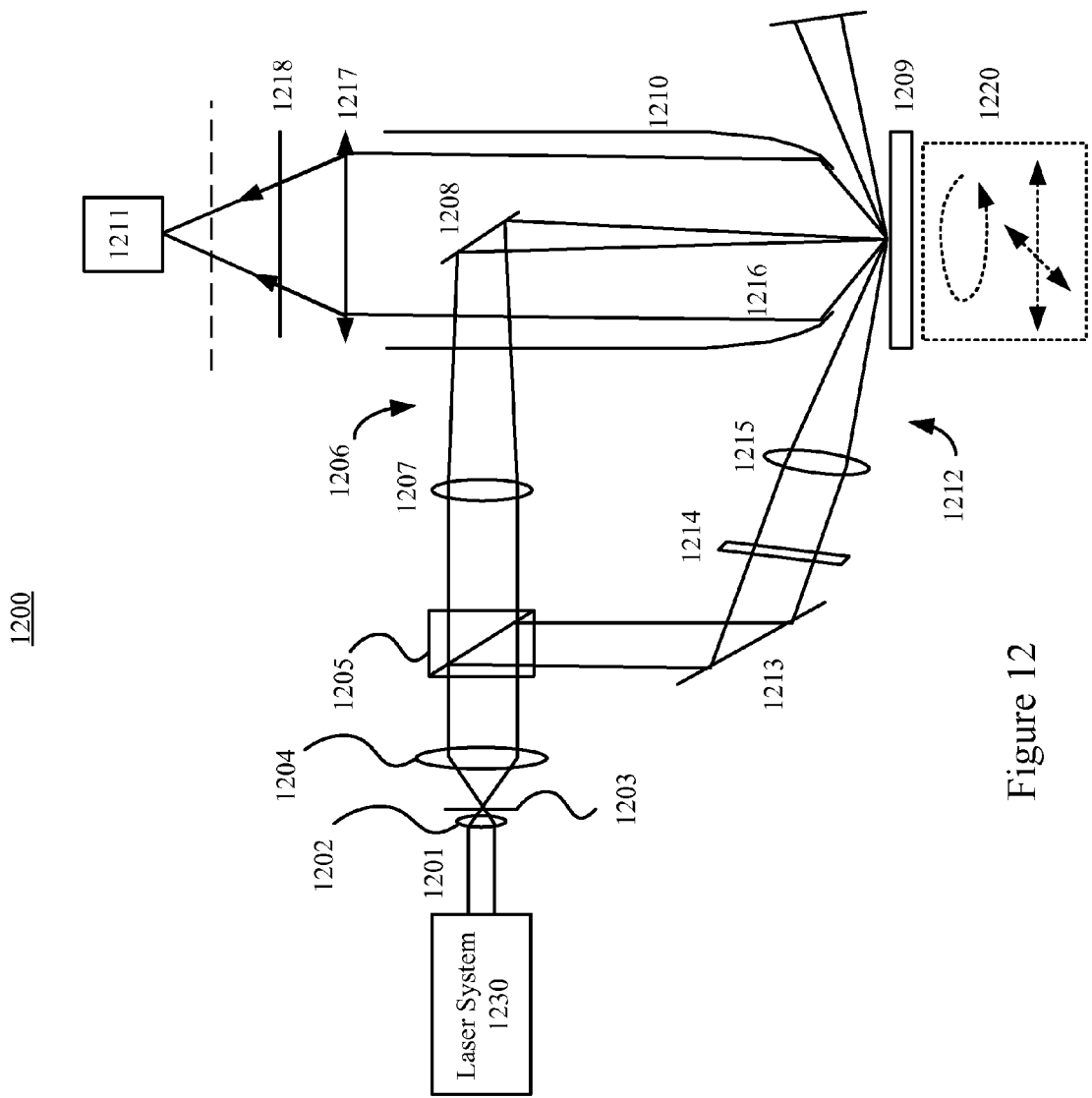
FIG. 12 illustrates an inspection system configured to implement anomaly detection using both normal and oblique illumination beams.

FIG. 12 illustrates an inspection system 1200 configured to implement anomaly detection using both normal and oblique illumination beams. In this configuration, a laser system 1230, which includes one of the 183 nm lasers described herein, can provide a laser beam 1201. A lens 1202 focuses the beam 1201 through a spatial filter 1203 and lens 1204 collimates the beam and conveys it to a polarizing beam splitter 1205. Beam splitter 1205 passes a first polarized component to the normal illumination channel and a second polarized component to the oblique illumination channel, where the first and second components are orthogonal. In the normal illumination channel 1206, the first polarized component is focused by optics 1207 and reflected by mirror 1208 towards a surface of a sample 1209. The radiation scattered by sample 1209 is collected and focused by a paraboloidal mirror 1210 to a detector or photomultiplier tube 1211.

In the oblique illumination channel 1212, the second polarized component is reflected by beam splitter 1205 to a mirror 1213 which reflects such beam through a half-wave plate 1214 and focused by optics 1215 to sample 1209.

Radiation originating from the oblique illumination beam in the oblique channel 1212 and scattered by sample 1209 is collected by paraboloidal mirror 1210 and focused to detector or photomultiplier tube 1211. Detector or photomultiplier tube 1211 has a pinhole or slit entrance. The pinhole or slit and the illuminated spot (from the normal and oblique illumination channels on surface 1209) are preferably at the foci of the paraboloidal mirror 1210.

The paraboloidal mirror 1210 collimates the scattered radiation from sample 1209 into a collimated beam 1216. Collimated beam 1216 is then focused by an objective 1217 and through an analyzer 1218 to the photomultiplier tube 1211. Note that curved mirrored surfaces having shapes other than paraboloidal shapes may also be used. An instrument 1220 can provide relative motion between the beams and sample 1209 so that spots are scanned across the surface of sample 1209. U.S. Pat. No. 6,201,601, which issued to Vaez-Iravani et al. on Mar. 13, 2001 and is incorporated by reference herein, describes inspection system 1200 in further detail.

Figure 13:
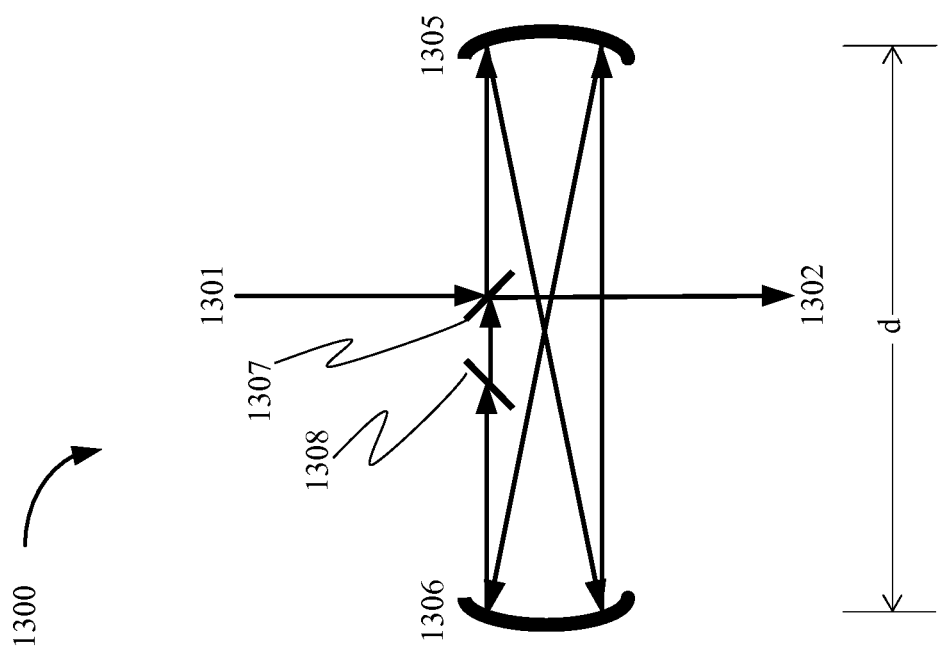
FIG. 13 illustrates an exemplary pulse multiplier for use with the above-described 183 nm laser in an inspection or metrology system.

FIG. 13 illustrates an exemplary pulse multiplier 1300 for use with the above-described 183 nm laser in an inspection or metrology system, such as one of the above described inspection systems. Pulse multiplier 1300 is configured to generate pulse trains from each input pulse 1301 from a 183 nm laser (not shown). Input pulse 1301 impinges on a beam splitter 1307. Part of each pulse is transmitted by a beam splitter 1307 in an output direction 1302 and part enters the ring cavity. As explained in U.S. patent application Ser. No. 13/711,593 (herein the '593 application), entitled "Semiconductor inspection and metrology system using laser pulse multiplier", filed by Chuang et al. on Dec. 11, 2012 and incorporated by reference herein, when used as a pulse-rate doubler, if the ring cavity and the beam splitter 1307 were lossless, then the beam splitter 1307 should preferably transmit about one third of the energy of each laser pulse and reflect about two thirds into the ring cavity. As explained in the '593 application, these transmission and reflection values can be modified to account for the beam splitter and cavity losses in order to maintain substantially equal energy output pulses in a pulse rate doubler.

After a laser pulse enters the ring cavity, it is reflected from a curved mirror 1305 and directed towards a curved mirror 1306. The mirror 1306 redirects the light back towards the mirror 1305. After multiple reflections from both mirrors (two reflections from each mirror in the example shown in FIG. 13), the pulse passes through compensator plate 1308 and arrives back at the beam splitter 1307. Compensator plate 1308 is intended to compensate for the displacement of the laser pulses as they transmit through beam splitter 1307 inside the ring cavity. Preferably compensator plate 1308 has substantially the same thickness and refractive index as beam splitter 1307. If compensator plate 1308 is placed in the same part of the ring cavity light path as the beam splitter 1307 (as shown), then compensator plate 1308 should preferably be oriented at an equal angle, but opposite direction, relative to the light path as the beam splitter 1307. Alternatively, the compensator plate 1308 may be placed in another part of the ring cavity at an appropriate orientation.

As explained in the '593 application, the ring cavity without beam splitter 1307 and compensator plate 1308 is similar to the ring cavities described in Herriott et al., "Off-axis Spherical Mirror Interferometers", Applied Optics 3, #4, pp 523-526 (1964) and in Herriott et al., "Folded Optical Delay Lines", Applied Optics 4, #8, pp 883-889 (1965). As described in these references, the number of reflections from each mirror depends only on the radius of curvature of the two mirrors relative to the separation of the mirrors d, and does not depend on the exact angle that the light enters the ring cavity. For example, if the radius of curvature of the two mirrors is d (i.e. the focal length of each mirror is d/2), then after two reflections from each mirror, each pulse will have been refocused and will arrive back at its starting point (beam splitter 1307 in FIG. 13). Herriott et al. (1964) give values for the focal length of the mirrors (and hence radius of curvature) as a multiple of d for 2, 3, 4, 6, 12 and 24 reflections off each mirror. As explained by Herriott et al. (1964), other numbers of reflections are possible. As described by Herriott et al. (1964), the reflections need not lie in one plane, depending on the number of reflections and the angle that the light is incident on the mirror 1305 from the beam splitter 1307. More than two reflections from each mirror make the cavity more compact compared with a cavity using two reflections from each mirror. However since some light is lost at each mirror reflection, two reflections per mirror will be preferred when mirror reflection losses are not so small (as, for example, at deep UV wavelengths), but more than two reflections per mirror may be usable when losses per reflection are small (for example at infra-red, visible or near UV wavelengths). Note that the length of the ring cavity, and thus the focusing of the ring cavity, can be adjusted by adjusting the distance d.

When a laser pulse arrives back at beam splitter 1307 after traversing the cavity, a part of the pulse will be reflected out of the ring cavity in the direction 1302 and part will be transmitted back into the ring cavity. The pulse multiplier 1300 will refocus the laser pulses regardless of the location of the beam waist of the input laser pulses, so that the output pulses leaving in the direction 1302 will appear to have approximately or substantially similar divergence and beam waist location as the input pulses. In some preferred embodiments of the pulse multiplier 1300, the input laser pulses from the direction 1301 will be substantially collimated so as to minimize the power density incident on the beam splitter 1307. The output laser pulses will then be substantially collimated also.

Periodically, a new input pulse 1301 is provided by the laser to pulse multiplier 1300. In one embodiment, the laser may generate approximately 0.015 nanosecond (ns) laser pulses at a repetition rate of approximately 80 MHz, and the cavity may double the repetition rate. Note that the optical path length of the ring cavity, and thus the delay of the ring cavity, can be controlled by choice of the distance d and the radius of curvature for the mirrors 1305 and 1306, which controls the number of reflections while ensuring refocusing of the laser pulses.

The ring cavity optical path length may be slightly greater than, or slightly less than, the nominal length calculated directly from the pulse interval divided by the multiplication factor. This results in the pulses not all arriving at exactly the same time at the polarized beam splitter and, so, slightly broadens the output pulse. For example, when the input pulse repetition rate is 80 MHz, the cavity delay would nominally be 6.25 ns for a frequency multiplication by 2. In one embodiment, a cavity length corresponding to a delay of 6.27 ns can be used so that the multiply reflected pulses do not arrive at exactly the same time as an incoming pulse. Moreover, the 6.27 ns cavity length for the 80 MHz input pulse repetition rate can also advantageously broaden the pulse and reduce pulse height. Other pulse multipliers having different input pulse rates or different multiplication factors can have different cavity delays.

More details of pulse multiplication and alternative pulse multipliers suitable for use with a 183 nm laser in inspection and metrology systems can be found in the above-cited '593 application, in U.S. patent application Ser. No. 13/487,075, entitled "Semiconductor Inspection And Metrology System Using Laser Pulse Multiplier" and filed on Jun. 1, 2012 by Chuang et al., and in U.S. patent application Ser. No. 14/596,738, entitled "Laser Pulse Multiplication Using Prisms" and filed on Jan. 14, 2015 by Chuang et al. All of these applications are incorporated by reference herein.

Figure 14:
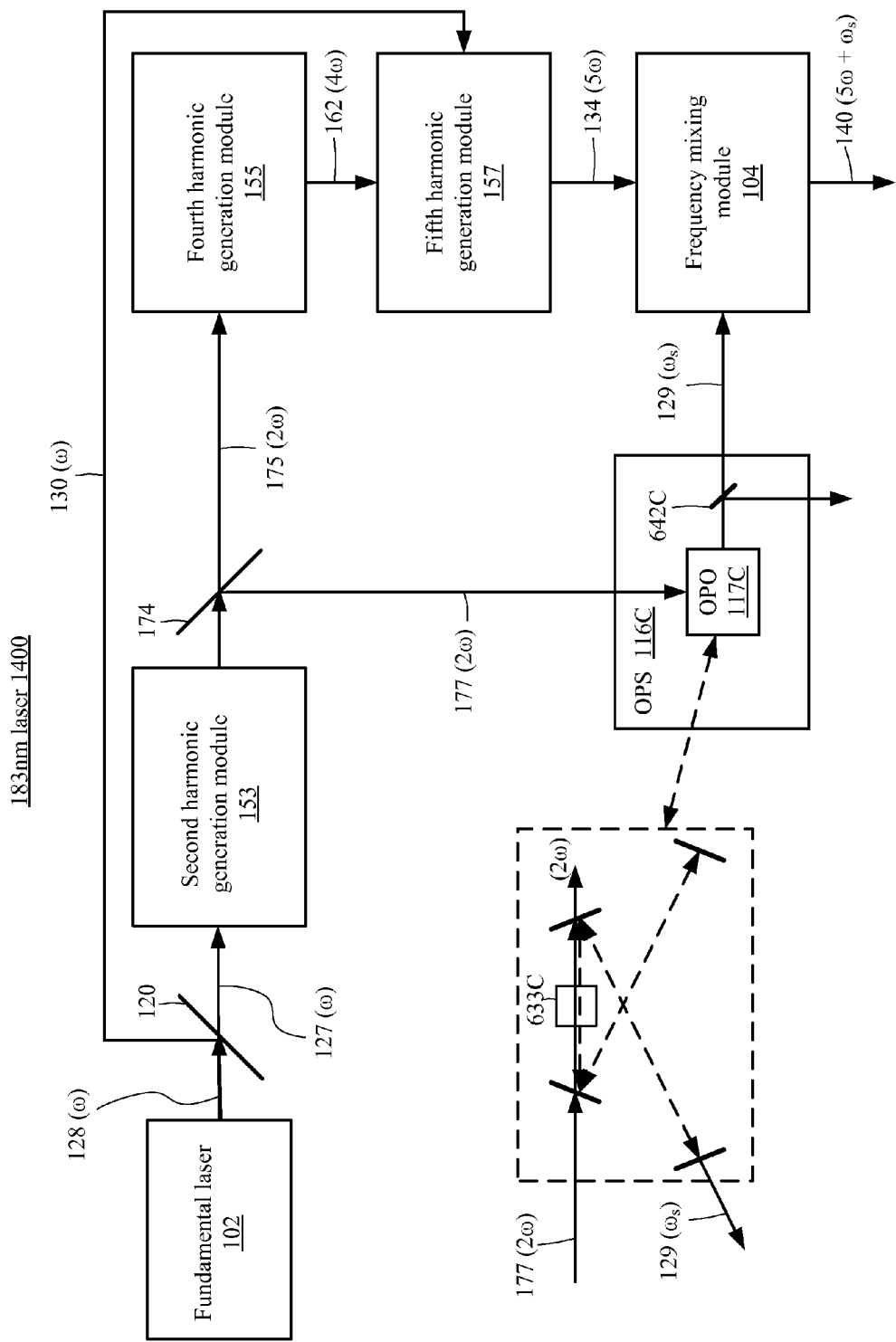
FIG. 14 is a simplified block diagram showing a 183 nm laser assembly according to another alternative embodiment of the present invention.

In addition to the solutions set forth above that generate 183 nm laser output light by way of generating down-converted signals using fundamental light, it is also possible to generate suitable down-converted signals by way of down-converting second harmonic light. For example, FIG. 14 shows a laser assembly 1400 including several of the same components utilized in the embodiments of FIGS. 1A and 1B, and thus are identified using the same reference numbers. Specifically, laser assembly 1400 includes a fundamental laser 102 configured to generate fundamental light 128 having a fundamental wavelength $\omega$, and utilizes a beam splitter 120 to divide fundamental light 128 into portions 127 and 130, where portion 130 is directed to a fifth harmonic generator 103C. Note that alternatively the portion 130 of the fundamental directed to the fifth harmonic generator may be taken from unconsumed fundamental from the output of the second harmonic generation module 153 in a manner similar to that depicted in FIG. 1B. In addition, similar to the approach shown in FIG. 1B, laser assembly 1400 includes a second harmonic generation module 153 and a fourth harmonic generation module 155 that generate second harmonic light 175 and fourth harmonic light 162 that is transmitted to fifth harmonic generation module 103C. Finally, laser assembly 1400 includes an OPS 116C that functions to generate down-converted signal 129 at a down-converted frequency $\omega_s$ such that, when down-converted signal 129 is subsequently mixed with fifth harmonic light 134 in a frequency mixing module 104, generates laser output light 140 in the range of approximately 180 nm and approximately 185 nm.

In accordance with the present embodiment, laser assembly 1400 differs from the embodiments of FIGS. 1A and 1B in that OPS 116C includes a "green-pumped" optical parametric oscillator (OPO) 117C that receives and down-converts a second harmonic light portion 177, which is divided from the output of second harmonic generation module 153 by way of a beam splitter 174. At the various frequencies of the common fundamental lasers mentioned above (i.e., having corresponding wavelengths ranging from 1030 nm to 1064 nm), a second harmonic frequency 2$\omega$ of second harmonic light portion 177 has corresponding wavelengths in the range of 515 nm to 532 nm, which is within the range typically associated with visible green light (i.e., 495 to 570 nm). As such, OPO 117C is "green-pumped" in the sense that its input is light in the visible green spectrum. As indicated in the dashed-line box in the lower left portion of FIG. 14, OPO 117C is otherwise constructed and configured in a manner similar to OPO 117E (discussed above) to down-convert second harmonic light portion 177 to a suitable down-converted signal frequency (e.g., 532 nm to approximately 1.3 µm). That is, other than non-linear crystal 633C (discussed below) the optical components forming the continuous-wave, singly resonant OPO arrangement utilized by OPO 117C are substantially identical to those described above with reference to OPO 117E, and as such their description is not repeated here for brevity. An advantage to this approach is that it avoids the need for a low-power seed signal (i.e., because the down-conversion of 532 nm light does not produce frequencies that are absorbed by most non-linear crystals), thus simplifying OPS 116C in that generation of down-converted signal 129 is achieved using only an OPO and an optional beam splitter 642C, which may be used to remove unwanted frequencies from down-converted signal 129 (as indicated in FIG. 14).

Although the green-pumped OPO approach utilized in laser assembly 1400 has been used to successfully generate down-converted signal 129 at down-converted frequencies $\omega_s$ (e.g., 1.3 µm) required to generate 183 nm output laser light using green-pumped OPO 117C, the use of second harmonic (green) light to generate down-converted signal 129 restricts the type of non-linear crystal that can be used in OPO 117C, and the conversion of green light is less efficient than the conversion of lower fundamental frequencies. That is, at high power levels, many of the preferred non-linear crystals (e.g., PPSLT) utilized with higher frequencies (e.g., OPO 117E; see FIG. 6B) are damaged by two-photon absorption of light in the visible green spectrum (e.g., 532 nm). To address this issue, green-pumped OPO 117C preferably implements non-linear crystal 633C using a lithium triborate (LBO) crystal because LBO crystals have a larger bandgap than lithium niobate or SLT, and thus are not subject to damage by high power at green light frequencies. However, even when an LBO crystal (or another green light tolerant crystal) is used in OPO 117C, the down-conversion of green light generates an undesirable approximately 900 nm photon for every 1.3 µm photon, so more than half the power that goes into OPO 117C is lost, making laser assembly 1400 less efficient than laser assemblies 100A and 100B (described above).

According to yet another possible embodiment, a laser assembly similar to that shown in FIG. 1A could be produced in which OPS 116 is replaced with a conventional OPO utilizing a lithium indium selenide (LISE) crystal. The inventors believe this approach ought to work because LISE crystals are believed not to strongly absorb frequencies around 6 µm, and thus should not significantly distort or undergo damage due to heating. However, LISE crystals are new, and the availability of sufficiently high quality LISE crystals is presently undeterminable.

The 183 nm laser described herein may be used in an inspection or metrology system in conjunction with optics to shape the pulses, reduce coherence or reduce speckle. Further details of the pulse-shaping, coherence, and speckle reducing apparatus and methods are disclosed in U.S. Pat. No. 9,080,990, issued on Jul. 14, 2015, and U.S. Pat. No. 9,080,991, also issued on Jul. 14, 2015. Both of these patents are incorporated by reference herein.

The various embodiments of the structures and methods described herein are illustrative only of the principles of the invention and are not intended to limit the scope of the invention to the particular embodiments described. For example, non-linear crystals other than CLBO, LBO, or BBO or periodically-poled materials can be used for some of the frequency conversion, harmonic generation and mixing stages.

The invention claimed is:

1. A laser assembly for generating laser output light having an output wavelength in the range of approximately 180 nm to approximately 185 nm, the laser assembly comprising:
   a fundamental laser configured to generate fundamental light having a fundamental wavelength equal to approximately 1064 nm and a corresponding fundamental frequency;

a second harmonic generator coupled to the fundamental laser such that the second harmonic generator receives a first portion of the fundamental light, said second harmonic generator being configured to generate second harmonic light having a second harmonic frequency equal to two times the fundamental frequency;

a fourth harmonic generation module coupled to receive a first portion of the second harmonic light and to generate fourth harmonic light having a fourth harmonic frequency equal to four times the fundamental frequency;

an optical parametric system (OPS) coupled to the fundamental laser such that said OPS receives a second portion of the second harmonic light, and said OPS is configured to generate a down-converted signal having a down-converted frequency that is less than the fundamental frequency;

a fifth harmonic generator coupled to the fundamental laser such that the fifth harmonic generator receives a second portion of the fundamental light and the fourth harmonic light, and said fifth harmonic generator is configured to generate fifth harmonic light having a fifth harmonic frequency equal to five times the fundamental frequency; and a frequency mixing module that is optically coupled to receive the down-converted signal from the OPS and the fifth harmonic light from the fifth harmonic generator, and configured to generate said laser output light by mixing said down-converted signal and said fifth harmonic light, wherein said fundamental laser is configured to generate said fundamental light such that said second portion of the second harmonic light comprises visible green light, wherein the OPS comprises a green-pumped optical parametric oscillator configured to generate said down-converted signal by down-converting said second portion of the second harmonic light, wherein the OPS is configured such that a sum of said down-converted frequency and said fifth harmonic frequency produces said laser output light in the range of approximately 180 nm to approximately 185 nm, wherein said down-converted signal has a down-converted wavelength corresponding to said down-converted frequency, wherein the green-pumped OPS comprises a first focusing mirror, a non-linear crystal, a second focusing mirror, a wavelength selector, and an output coupler that are operably configured to form a cavity in which light is reflected between said wavelength selector and said output coupler by way of said first and second focusing mirrors and said non-linear crystal, wherein said wavelength selector is configured to be highly reflective for light having wavelengths in a wavelength range of approximately 0.2 nm of said down-converted wavelength, wherein said output coupler is configured to pass a portion of said light reflected between said wavelength selector and said output coupler as said down-converted signal, and wherein said non-linear crystal comprises a lithium triborate (LBO) crystal.

2. The laser assembly of claim 1, wherein at least one of the fifth harmonic generator and the frequency mixing module comprises one of an annealed CLBO crystal, a deuterium-treated CLBO crystal and a hydrogen-treated CLBO crystal.

3. The laser assembly of claim 1, wherein said green pumped optical parametric system is configured such that the down-converted signal has a signal wavelength in the range of approximately 1250 nm to approximately 1830 nm.

4. The laser assembly of claim 3, wherein the fundamental laser comprises one of a mode-locked laser, a quasi-continuous-wave laser, laser diode and a fiber laser.

5. An inspection system comprising:

a laser assembly configured to generate laser output light having an output wavelength in the range of approximately 180 nm to approximately 185 nm;

first optics configured to direct the laser output light from the laser assembly to an object being inspected;

second optics configured to collect an image portion of said laser output light affected by the object being inspected, and to direct the image portion to one or more sensors, wherein the laser assembly comprises:

a fundamental laser configured to generate fundamental light having a fundamental wavelength equal to approximately 1064 nm and a corresponding fundamental frequency;

a second harmonic generator coupled to the fundamental laser such that the second harmonic generator receives a first portion of the fundamental light, said second harmonic generator being configured to generate second harmonic light having a second harmonic frequency equal to two times the fundamental frequency;

a fourth harmonic generation module coupled to receive a first portion of the second harmonic light and to generate fourth harmonic light having a fourth harmonic frequency equal to four times the fundamental frequency;

an optical parametric system (OPS) coupled to the fundamental laser such that said OPS receives a second portion of the second harmonic light, and said OPS is configured to generate a down-converted signal having a down-converted frequency that is less than the fundamental frequency;

a fifth harmonic generator coupled to the fundamental laser such that the fifth harmonic generator receives a second portion of the fundamental light and the fourth harmonic light, and said fifth harmonic generator is configured to generate fifth harmonic light having a fifth harmonic frequency equal to five times the fundamental frequency; and a frequency mixing module that is optically coupled to receive the down-converted signal from the OPS and the fifth harmonic light from the fifth harmonic generator, and configured to generate said laser output light by mixing said down-converted signal and said fifth harmonic light, wherein said fundamental laser is configured to generate said fundamental light such that said second portion of the second harmonic light comprises visible green light, wherein the OPS comprises a green-pumped optical parametric oscillator configured to generate said down-converted signal by down-converting said second portion of the second harmonic light, wherein the OPS is configured such that a sum of said down-converted frequency and said fifth harmonic frequency produces said laser output light in the range of approximately 180 nm to approximately 185 nm, wherein said down-converted signal has a down-converted wavelength corresponding to said down-converted frequency, wherein the OPS comprises a first focusing mirror, a non-linear crystal, a second focusing mirror, a wavelength selector, and an output coupler that are operably configured to form a cavity in which light is reflected between said wavelength selector and said output coupler by way of said first and second focusing mirrors and said non-linear crystal, wherein said wavelength selector is configured to be highly reflective for light having wavelengths in a wavelength range of approximately 0.2 nm of said down-converted wavelength, wherein said output coupler is configured to pass a portion of said light reflected between said wavelength selector and said output coupler as said down-converted signal, and wherein said non-linear crystal comprises a lithium triborate (LBO) crystal.

6. The inspection system of claim 5, wherein the inspection system comprises a dark-field inspection system.

7. The inspection system of claim 5, further comprising at least one of an acousto-optic modulator and an electro-optic modulator configured to reduce coherence of the laser output light directed to the object being inspected.

8. The inspection system of claim 5, further comprising a pulse rate multiplier configured to increase a pulse repetition rate of the laser assembly.

9. The inspection system of claim 5, wherein said second optics are configured to simultaneously direct a reflected image portion and a transmitted image portion to a single sensor.

10. The inspection system of claim 5, wherein the first optics comprises one or more components configured to direct the laser output light such that said laser output light forms an illuminated line on said object being inspected.

11. The inspection system of claim 5, wherein the first optics comprises one or more components configured to direct the laser output light such that said laser output light forms multiple, simultaneously-illuminated spots on said object being inspected.

12. The inspection system of claim 5, wherein said optical parametric system is configured such that the down-converted signal has a signal wavelength in the range of approximately 1250 nm to approximately 1830 nm.

13. The inspection system of claim 12, wherein the fifth harmonic generator comprises at least one of an annealed CLBO crystal, a deuterium-treated CLBO crystal and a hydrogen-treated CLBO crystal.

* * * * *